United States Patent [19]

Rodriguez

[11] Patent Number: 5,693,506
[45] Date of Patent: Dec. 2, 1997

[54] PROCESS FOR PROTEIN PRODUCTION IN PLANTS

[75] Inventor: Raymond L. Rodriguez, Davis, Calif.

[73] Assignee: The Regents of the University of California, Oakland, Calif.

[21] Appl. No.: 153,563

[22] Filed: Nov. 16, 1993

[51] Int. Cl.$^6$ .................. C12N 15/09; C12N 15/29; C07H 21/04; A01H 1/00; A01H 1/04
[52] U.S. Cl. ............. 435/172.3; 536/23.6; 536/25.3; 536/23.4; 536/24.1; 800/205; 800/250; 435/69.8; 435/204
[58] Field of Search .................. 435/172.3, 172.1, 435/69.8, 204; 800/200, 205, 250, DIG. 57; 536/25.5, 23.6, 22.1, 23.4, 24.1, 25.3

[56] References Cited

FOREIGN PATENT DOCUMENTS

WO 91/13993  9/1991  WIPO.

OTHER PUBLICATIONS

Baulcombe, D.C., et al., "A novel wheat α-amylase gene (α-Amy3)," *Mol. Gen. Genet.* 209: 33–40 (1987).

Benkel, B.F., and D.A. Hickey, "A Drosophilia gene is subject to glucose repression," *Proc. Natl. Acad. Sci. USA* 84: 1337–1339 (1987).

Chandler, P.M., et al., "The effects of gibberellic acid and abscisic acid on α-amylase mRNA levels in barley aleurone layers studies using an α-amylase cDNA clone," *Plant Molecular Biology* 3: 407–418 (1984).

Hintz, W.E., and P.A. Lagosky, "A Glucose-Derepressed Promoter for Expression of Heterologous Products in the Filamentous Fungus Aspergillus nidulans," *Bio/Technology* 11: 815–818 (1993).

Huang, N., et al., "Structural organization and differential expression of rice α-amylase genes," *Nucleic Acids Research* 18(23): 7007–7014 (1990).

Huang, N., et al., "Classification and evolution of α-amylase genes in plants," *Proc. Natl. Acad. Sci. USA.* 89: 7526–7530 (1992).

Huang, N., et al., "Classification and characterization of the rice α-amylase multigene family," *Plant Molecular Biology* 14: 655–668 (1990).

Huang, N., et al., "RAmy2A; a novel α-amylase-encoding gene in rice," *Gene* 111: 223–228 (1992).

Jones, R.L., and J. MacMillan, "Gebberellins," in *Advanced Plant Physiology*, Malcolm B. Wilkins, ed., Pitman Publishing Limited, London, pp. 21–52 (1984).

Knudsen, S., and M. Muller, "Transformation of the developing barley endosperm by particle bombardment," *Planta* 185: 330–336 (1991).

Maas, C., et al., "Applications of an optimized monocot expression vector in studying transient gene expression and stable transformation of barley," *Physiologia Plantarum* 85: 367–373 (1992).

Maas, C., et al., "A feedback control element near the transcription start site of the maize Shrunken gene determines promoter activity," *The EMBO Journal* 9(11): 3447–3452 (1990).

Pen, J., et al., "Phytase-containing Transgenic Seeds as a Novel Feed Additive for Improved Phosphorus Utilization," *Bio/Technology* 11: 811–814 (1993).

Ritala, A., et al., "Stable transformation of barley tissue culture by particle bombardment," *Plant Cell Reports* 12: 435–440 (1993).

Rodriguez, R.L., et al., "Organization, structure, and expression of the rice α-amylase multigene family," *Rice Genetics* 11: 417–429 (1990).

Rogers, J.C., "Two Barley α-Amylase Gene Families are Regulated Differently in Aleurone Cells," *The Journal of Biological Chemistry* 260(6): 32731–3738 (1985).

Rothstein, S.J., et al., "Synthesis and secretion of wheat α-amylase in *Saccharomyces cerevisiae*," *Gene* 55: 353–356 (1987).

Sheen, J., "Metabolic Repression of Transcription in Higher Plants," *The Plant Cell* 2: 1027–1038 (1990).

Simmons, C.R., and R.L. Rodriguez, "High–Level Synthesis and Secretion of α-Amylase from Rice Callus," Chapter 14 from *Biocatalysis in Agricultural Biotechnology* (Whitaker, J.R., and P.E. Sonnet, eds., American Chemical Society, Washington, D.C., 1989, pp. 202–214).

Sutliff, T.D., et al., "Characterization of an α-amylase multi-gene cluster in rice," *Plant Molecular Biology* 16: 579–591 (1991).

Whittier, R.F., et al., "Nucleotide sequence analysis of alpha-amylase and thiol protease genes that are hormonally regulated in barley aleurone cells," *Nucleic Acids Research* 15(6): 2515–2535 (1987).

Wilmink, A., and J.J.M. Dons, "Selective Agents and Marker Genes for Use in Transformation of Monocotyledonous Plants," *Plant Molecular Biology Reporter* 11(2): 165–185 (1993).

Wirsel, S., et al., "Three α-amylase genes of *Aspergillus oryzae* exhibit identical intron–exon organization," *Molecular Microbiology* 3(1): 3–14 (1989).

Yu, S.-M., et al., "Regulation of α-amylase-encoding gene expression in germinating seeds and cultured cells of rice," *Gene* 122: 247–253 (1992).

Zenk, M.H., "T. Chasing the enzymes of secondary metabolism: Plant cell cultures as a pot of gold," *Phytochemistry* 30(12): 3861–3863 (1991).

Huang et al. 1990. Plant Molecular Biology. 14:655–668.
Jacobson et al. 1991. Plant Molecular Biology. 16:713–724.
Rogers. 1985. The Journal of Biological Chemistry. 260(6): 3731–3738.

*Primary Examiner*—David T. Fox
*Assistant Examiner*—Erich E. Veitenheimer
*Attorney, Agent, or Firm*—Gary R. Fabian; Peter J. Dehlinger

[57] ABSTRACT

This invention provides for the secretion of heterologous protein in plant systems. In particular, this invention provides for the production of heterologous proteins in plant cultures and seeds. Where seeds are the source of the protein, the heterologous genes are expressed during germination and isolated from a malt.

8 Claims, 11 Drawing Sheets
(1 of 11 Drawings in Color)

AVERAGE GUS ACTIVITY (nM/min/mg)

| RAmy 3D | -264 | GAGACCGGGCCCCGACGCGGCCGACGCGGCG | (SEQ ID NO: 3) |
| RAmy 3E | -392 | GAGAGCTCGCGCCGCCTCGATCGGCGCGGCG | (SEQ ID NO: 4) |

| RAmy 3D | -648 | TTCCGGCTGC | (SEQ ID NO: 5) |
| RAmy 3E | -479 | TTGCGGCTTGC | (SEQ ID NO: 6) |

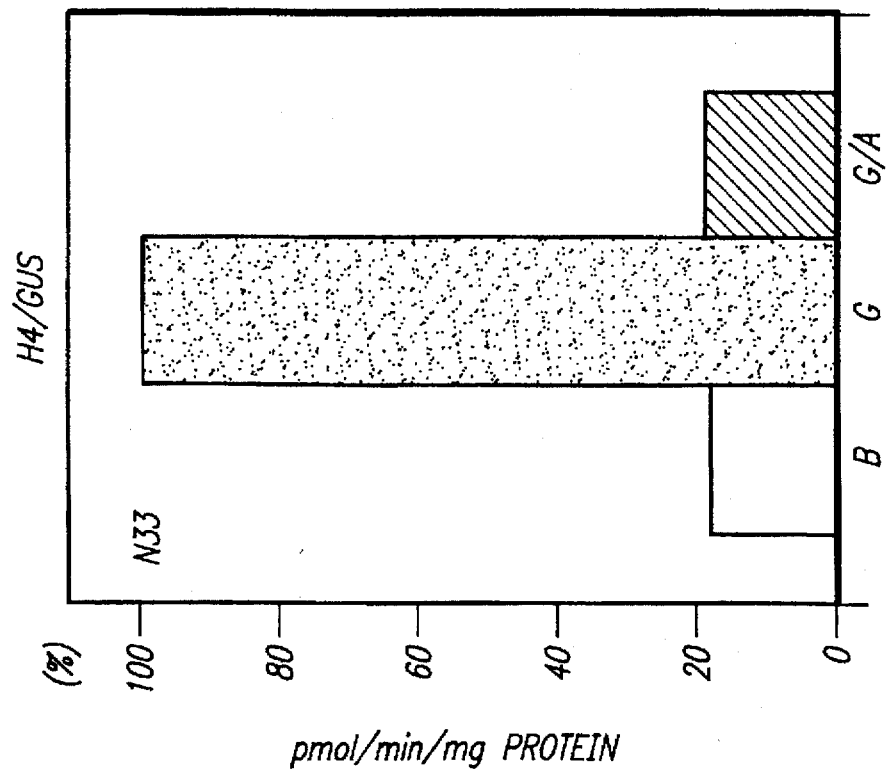
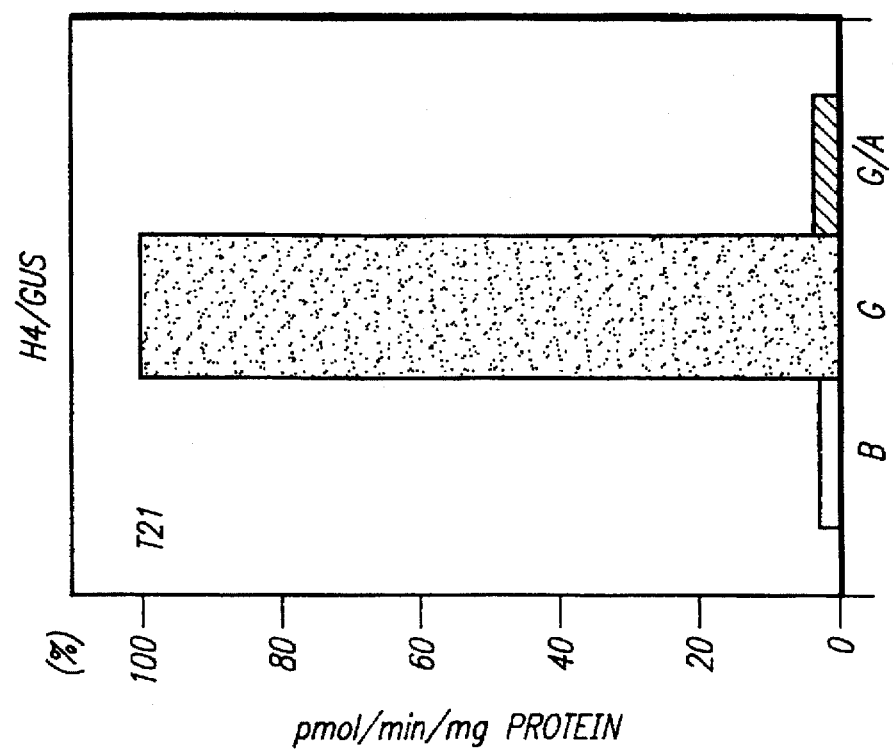

PROCESS FOR PROTEIN PRODUCTION IN PLANTS

TECHNICAL FIELD

The field of this invention is production of proteins in plants.

BACKGROUND OF THE INVENTION

With the advent of recombinant technology, the ability to clone and produce a wide range of proteins from diverse sources became feasible. The selection of expression hosts for commercial biotechnology proteins is based on the economics of fermentation and purification as well as the ability of the host to accomplish the post-translational modifications needed for full biological activity of the recombinant protein. Some of these post-translational modifications include: signal peptide processing, propeptide processing, protein folding, disulfide bond formation, glycosylation, gamma carboxylation and beta-hydroxylation. Some of the economic factors influencing the choice of an expression host include: rates of biomass production, equipment costs, medium composition and expense, processes for protein recovery and purification, product yields, and the potential for contamination.

Much of the early work in biotechnology was directed toward the expression of recombinant or "heterologous" proteins in prokaryotes like *Escherichia coli* and *Bacillus subtilis* because of the ease of genetic manipulation and growth in batch culture and large-scale fermentation. Today, commercial production of recombinant proteins is achieved using a variety of eukaryotic host organisms in addition to prokaryotes like *E. coli* and *B. subtilis*. Although *E. coli* can perform signal peptide processing, protein folding, and disulfide bond formation, it can not secrete proteins extracellularly nor can it glycosylate, gamma carboxylate, beta hydroxylate or process propeptides. *B. subtilis* suffers from the same limitations *E. coli* except that it is capable of extracellular secretion.

Total production costs from bacteria are also high because of problems with product recovery, purification, and the inability of bacteria to perform many of the post-translational modifications mentioned above. Furthermore, *E. coli* and other bacteria are pathogens and contaminants such as pyrogens and endotoxins must be removed from the recombinant protein. In addition, extensive post-purification chemical and enzymatic treatments (e.g., to refold the protein into an active form) can be required to obtain biologically active protein. Because proteins are not secreted from prokaryotes like *E. coli*, bacterial cells must be disrupted for product recovery. The subsequent release of bacterial contaminants and other proteins make product purification more difficult and expensive. Because purification accounts for up to 90% of the total cost of producing recombinant proteins in bacteria, protein like tissue Plasminogen Activator (tPA) can cost several thousand dollars per gram to produce from *E. coli*.

Because of the many inadequacies associated with prokaryotic hosts, the biotechnology industry has looked to eukaryotic hosts like mammalian cell tissue culture, yeast, fungi, insect cells, and transgenic animals, to properly and efficiently express recombinant proteins. However, these hosts can suffer from any or all of the following disadvantages: expensive fermentation, low yields, secretion problems, inappropriate modifications in protein processing, high operating costs, difficulties in scaling up to large volumes, and/or contamination that either kills the host culture or makes product purification more expensive. For these reasons, existing eukaryotic hosts are unable to provide high-volume, low-cost protein production of recombinant proteins.

For most of those proteins requiring extensive post-translational modifications for therapeutic and/or functional activity, mammalian cell culture is the most common alternative to *E. coli*. Although mammalian cells are capable of correctly folding and glycosylating bioactive proteins, the quality and extent of glycosylation can vary with different culture conditions among the same host cells. Furthermore, mammalian culture has extremely high fermentation costs (60–80% of total production expense), requires expensive media, and poses safety concerns from potential contamination by viruses and other pathogens. Yields are generally low and in the range of 0.5–1.5% of cellular protein, or micrograms per liter (up to 300–400 milligrams per liter).

Yeast, fungi, insect cells and transgenic animals are currently being used as alternatives to mammalian cell culture. Yeast, however, produces incorrectly glycosylated proteins that have excessive mannose residues and generally limited eukaryotic processing. Further, although the baculovirus insect cell system can produce high levels of glycosylated proteins, these are not secreted—making purification complex and expensive. Fungi represent the best current system for high-volume, low-cost production, but they are not capable of expressing many target proteins. Transgenic animals are subject to lengthy lead times to develop herds with stable genetics, high operating costs, and contamination by animal viruses.

The biochemical, technical and economic limitations on existing prokaryotic and eukaryotic expression systems has created substantial interest in developing new expression systems for recombinant proteins. Plants represent the most likely alternative to existing systems because of the advantageous economics of field-grown crops, the ability to synthesize proteins in storage organs like tubers, seeds, fruits and leaves and the ability of plants to perform many of the post-translational modifications previously described. However, existing plant expression systems suffer from low yield (<1.5% of total cellular protein). Furthermore, expression of the target protein occurs in the open field (in roots, stems, leaves, fruits and seeds), thus making it difficult to prevent the recombinant protein from entering the food and feed chain. This is an issue of much concern to government regulatory agencies.

Although the use of plant cell culture to express proteins has been discussed, the lack of knowledge about the genetics and biochemistry of plant gene expression and secretion has precluded this system from being developed into a commercially feasible one. Therefore, plant systems that could express high levels of recombinant protein at low cost, in a controlled and contained fashion, would be a valuable addition to the biotechnology industry. The regulated expression of recombinant proteins in malted cereal seeds and cereal cell culture represents such a system. Malting is the process by which gain, typically barley, is germinated under controlled conditions and in contained facilities to produce a product that can be used for human consumption, animal feed and the brewing of alcoholic beverages. The process begins by steeping barley seeds in 55° F. water for 48 hours followed by a four-day germination of the grain in malting bins or drums. During this time, the starchy portion of the seed, or endosperm, is converted to maltose and other sugars. Maltsters use water, air and, in some instances, phytohormones like gibberellic acid to control temperature and optimize the malting process. The malted grain is then kiln-dried at temperatures between 120 F. and 130 F. to terminate germination and remove moisture. At this point the malted grain can be stored or sold to the food, feed or brewing industries. In the malting process, the rapid conversion of starch to sugar is accomplished by a tremendous burst of gene activity that results in the expression of a starch degrading enzyme called α-amylase. During the peak stage of germination, α-amylase is the major protein in the seed, constituting up to 60% of the total protein of the cells that surround the starchy endosperm. Alpha-amylase is secreted out of these cells and into the endosperm where it digests the starch into sugar. Expression and secretion of α-amylase during germination is so abundant that it can be purified and sold as a research reagent for approximately $0.10 per gram. The ability to genetically engineer cereal grains like rice, wheat and barley now makes if possible to develop a low-cost, high-volume eukaryotic expression system based on the malting of transgenic seeds.

Relevant Literature

The potential for the use of plant cell cultures to product proteins has been described by Zenk, *Phytochemistry* 30:3861–3863 (1991). Descriptions of the rice amylase genes may be found in Huang et al., *Proc. Marl. Sci. U.S.A.* 89:7526–7530 (1992); Huang et al., *Plant, Molecular Biology* 14:655–668 (1990); Huang et al., *Nucleic Acids Research* 18:7007–7014 (1990); Huang et al., *Gene* 11 1:223–228 (1992); Rodriguez et al.: Organization Structure and Expression of the Rice α-Amylase Multigene Family. *Second International Rice Genetics Symposium. Rice Genetics* 11:417–429 (1990); Sutliff et al., *Plant Molecular Biology* 16:579–591 (1991). The promoter sequences for the rice amylase genes are described in Huang et al., *Nucleic Acids Research* 18:7007–7014 (1990). Descriptions of plant protein signal peptides may be found in addition to the references described above in Vaulcombe et al., *Mol. Gen. Genet.* 209:33–40 (1987); Chandler et al., *Plant Molecular Biology* 3:407–418 (1984); Rogers, *J. Biol. Chem.* 260:3731–3738 (1985); Rothstein et al., *Gene* 55:353–356 (1987); Whittier et al., *Nucleic Acids Research* 15:2515–2535 (1987); Wirsel et al., *Molecular Microbiology* 3:3–14 (1989); Yu et al., *Gene* 122:247–253 (1992).

A description of the regulation of plant gene expression by the phytohormone, gibberellic acid and secreted enzymes induced by gibberellic acid can be found in R. L. Jones and J. MacMillin, Gibberellins: in: *Advanced Plant Physiology,*. Malcolm B. Wilkins, ed., 1984 Pitman Publishing Limited, London, pp. 21–52. References that describe other metabolically-regulated genes: Sheen, *Plant Cell,* 2:1027–1038(1990); Maas et al., *EMBO J.* 9:3447–3452 (1990); Benkel and Hickey, *Proc. Natl. Acad. Sci.* 84:1337–1339 (1987)

SUMMARY OF THE INVENTION

A two-step process for producing recombinant proteins in cereal seeds and cell cultures derived from cereal plants, is provided. Genes encoding recombinant proteins are inserted into two separate expression constructs. One construct uses metabolically regulated promoters to achieve expression of the recombinant protein in plant cell culture or, during germination (i.e., malting) of transgenic seed. The other expression construct uses a hormonally regulated promoter to achieve expression of the recombinant protein in the malted seed. Both constructs utilize additional regulatory DNA sequences that permit the target protein to be secreted extracellularly. Cells or tissues derived from cereal plants can be transformed singly or together (i.e., co-transformation) with the expression constructs. Transgenic callus tissue derived from these transformation events are used to express the recombinant protein in cell culture. The resulting transgenic calli can also be used to regenerate whole transgenic plants that produce viable seeds. Using this two-step process, the recombinant protein can be recovered and purified first, from the cell culture medium and second, from the mash (seed protein extract) from malted transgenic seeds. Expression of recombinant proteins in the malting system can be further maximized by modifying the malting process to accommodate dehulled, de-embryonated seeds and isolated embryos.

The file of this patent contains at least one photograph executed in color. Copies of this patent with color photograph(s) will be provided by the Patent and Trademark Office upon request and payment of necessary fee.

BRIEF DESCRIPTION OF THE DRAWINGS

FIG. 1A represents expression results obtained using a RAmy3D promoter/GUS fusion construct.

FIG. 1B represents expression results obtained using a RAmy1A promoter/GUS fusion construct.

FIG. 3A depicts DNA isolated from 3DG cells and probed with a GUS gene probe. Equivalent amounts of DNA were detected in all lanes when the same membrane was stripped of the GUS probe and rehybridized with a probe from the rice α-amylase gene RAmy1A (FIG. 3B).

FIG. 7A depict the construct of two gene fusions used to express GUS in rice seed.

FIGS. 7B and C are the results of southern blots demonstrating the stable transmission of the GUS gene to rice progeny.

FIGS. 10A, 10B, 10C and 10D provide graphic depictions of fluorometric measures of the expression of GUS in four transgenic seed lines quantifying the induction of GUS by addition of giberellic acid.

DEFINITIONS

Figure 1A:
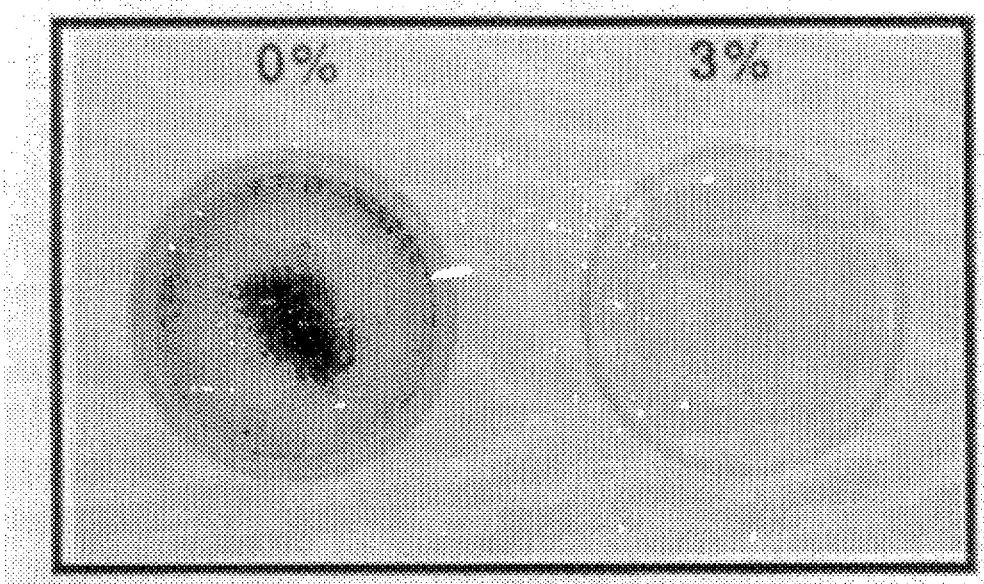
FIGS. 1A and 1B are full color photographs of the expression of the GUS gene in cell culture (1A) and seed (1B).

"Cell culture" refers to cells and cell clusters both protoplast and callus tissue that without differentiated cells or organs and is growing on a growth media.

"In an amount effective" refers to an amount that is suitable to produce the desired effect in a measurable and reproducible amount.

"Inducible" means a promoter that is turned on by the presence or absence of a cell hormone or metabolite. It includes both indirect and direct inducement.

"Inducible during germination" refers to promoters which are substantially silent but not totally silent prior to germination but are turned on substantially (greater than 25%) during germination.

"Operably linked" refers to components of an expression cassette that function as a unit to express a heterologous protein.

"Removal" in the context of a metabolite includes both physical removal as by washing and the depletion of the metabolite through the absorption and metabolizing of the metabolite by the cells.

"Signal sequence suitable to permit the heterologous protein to be secreted across the aleurone or scutellular epithelium" refers to any naturally occurring signal sequence in monocots, dicots, animals or microorganisms that can permit a protein to be secreted from the cells across the stated organs of the monocot seed.

DETAILED DESCRIPTION

This patent describes a two-step process for the low-cost, high level expression of recombinant proteins in genetically modified (i.e., transformed) plant cell culture and/or germinated (i.e., malted) transgenic seeds. The plants (including organs, seeds, tissues and cells) used in this process are derived from monocots, particularly the members of the taxonomic family known as the Gramineae. This family includes all members of the grass family of which the edible varieties are known as cereals. The cereals include a wide variety of species such as wheat (Triticum sps.), rice (Oryza, sps.) barley (Hordeum sps.) oats, (Avena sps.) rye (Secale sps.), corn (Zea sps.) and millet (Pennisettum sps.).

Plant cells or tissues derived from the members of the Gramineae are transformed with two expression constructs (i.e., plasmid DNA into which the gene of interest has been inserted) using a variety of standard techniques (e.g., electroporation, protoplast fusion or microparticle bombardment). In one of the expression constructs, the gene encoding the recombinant protein is placed under the control of a metabolically regulated promoter. Metabolically regulated promoters are those in which mRNA synthesis or transcription, is repressed or induced by sugars or sugar derivatives. Examples of metabolically regulated promoters include those that transcribe some of the cereal α-amylase genes and sucrose synthase genes.

The other expression construct uses a hormonally regulated promoters to achieve expression of the recombinant protein in the germinated or malted seed. Hormonally regulated promoters are those in which mRNA synthesis or transcription, is repressed or induced by phytohormones such as gibberellic acid or abscisic acid. Examples of hormonally regulated promoters include those that transcribe some of the cereal α-amylase genes. The promoters relevant to this application include, but are not limited to, those controlling the expression of the rice (*Oryza sativa*) α-amylases genes, RAmy1A, RAmy3D and RAmy3E, the barley α-amylase gene promoter, HV18 and the sucrose synthase and sucrose-6-phosphate-synthetase (SPS) promoters from rice and barley. Both construct utilize additional regulatory DNA sequences (i.e., signal peptide sequences and preferred translational start codons) to promote efficient translation and extracellular secretion of the target protein. By fusing the genes for recombinant proteins to this array of regulatory DNA sequences, the expression of recombinant proteins in transgenic callus tissue or germinated transgenic seeds is placed under the transcription and secretion control of a metabolically regulated or hormonally regulated promoter.

Figure 1B:

Cells or tissues or derived from cereal plants can be transformed singly or together (i.e., co-transformation) with the expression constructs. Once integrated into the plant genome, the recombinant protein can be recovered and purified first, from the cell culture medium and second, from the mash (seed protein extract) from malted transgenic seeds. The principle of using different cereal a-amylase promoters to express a recombinant protein in plant cell culture and in transgenic seeds is illustrated in FIGS. 1A and 1B. In this figure, the sugar-repressible promoter for the rice α-amylase gene, RAmy3D, and the gibberellic acid-induced promoter for the RAmy1A gene, were used to express the bacterial reporter gene, gusA, in rice. The gusA gene encodes the enzyme, beta-glucuronidase (GUS), that produces a blue chromophore in tissues expressing the gene. This chromophore can be easily detected using a histochemical staining method. As can been seen in this figure, the product of gusA is repressed in rice cells when the culture medium contains 3% sugar. In transgenic rice seeds containing the RAmy1A promoter/GUS fusion, the blue chromophore increases up to six days of germination. Using this two-step expression system, cereal species such as rice, corn, wheat, oats, rye, barley and various grasses can be genetically engineered to express a wide range of recombinant proteins in either or both stages. By combining this unique technology with well-established production methods (e.g., plant cell fermentation, crop cultivation, malting, and product recovery), recombinant protein can be efficiently and economically produced for the biopharmaceutical, industrial processing, animal health and bioremediation industries. The fact that this expression system does not require the use of genetic elements derived from animal or plant pathogens should facilitate regulatory acceptance.

A. General Methods

Generally, the nomenclature and general laboratory procedures with respect to recombinant DNA technology can be found in Sambrook, et al., *Molecular Cloning—A Laboratory Manual*, Cold Spring Harbor Laboratory, Cold Spring Harbor, N.Y. 1989 and in S. B. Gelvin and R. A. Schilperoot, *Plant Molecular Biology,* 1988. Other general references are provided throughout this document. The procedures therein are well known in the art and are provided for the convenience of the reader. All the information contained therein is incorporated herein by reference.

B. General Sources of promoter and signal sequences

By using a number of standard procedures, one of skill can identify suitable promoters and signal sequences for use in this invention in other species of plants. While the gene can be amplified directly from a mRNA extract using PCR, the first step is generally to produce a genomic or cDNA library.

In brief, genomic or cDNA libraries are prepared according to standard techniques as described, for instance, in Sambrook, supra. To construct genomic libraries, large segments of genomic DNA are generated by random fragmentation and are ligated with vector DNA to form concatemers that can be packaged into the appropriate vector. Two kinds of vectors are commonly used for this purpose, bacteriophage lambda vectors and cosmids.

In the present invention, cDNA libraries enriched for α-amylase secreting mRNA sequences are generally used to screen for the desired genes. Preparation of appropriately enriched cDNA would involve the use of plant organs over expressing and secreting α-amylase, e.g. aleurone layers. Other organs would include roots, stems, leaves and panicles. Briefly, mRNA from select tissue is isolated and cDNA is prepared. Short chains of oligo d-T nucleotides are hybridized with the poly-A tails of the mRNA and serve as a primer for the enzyme, reverse transcriptase, which synthesizes a complementary DNA (cDNA) strand. The cDNA can be optionally enriched for the desired sequences using subtraction hybridization procedures by labelling the cDNA and hybridizing it with mRNA from tissue that does not express the desired mRNA according to the procedures. *Proc. Natl. Acad. Sci. U.S.A.* 81:2194–2198 (1984).

Unreacted cDNA is isolated and used to prepare a library for screening. To do this, a second DNA strand is synthesized using the first cDNA strand as a template. Linkers are added to the double-stranded cDNA for insertion into a plasmid or λ phage vector for propagation in *E. coli*.

Identification of clones harboring the desired sequences is performed by either nucleic acid hybridization or immunological detection of the encoded protein, if an expression vector is used. Typically, oligonucleotide probes specific for known promoters and signal peptides are used. Alternatively, the cDNA clone can be used as a probe to screen the genomic library. Genomic clones isolated with this approach will contain gene sequences that include the promoter, coding region, introns and terminators.

Oligonucleotide and cDNA probes useful for identification of other promoters and signal sequences can also be prepared from conserved regions of related genes in other species. By comparing the nucleotide sequences of the known proteins, one simply identifies conserved sequences in the genes and uses those sequences as probes or as PCR primers to locate homologous sequences in genomic or cDNA libraries of other plants. A number of references compare regions of nucleotide homology and amino acid identity regarding secreting genes and they are provided below. Such conserved sequences and can be used to isolate other genes having a hormonal or other metabolite responsive promoter.

Probes, typically used to identify related but heretofore unknown target sequences, are hybridize under stringent conditions to ensure that the sequences are in fact related. Typically, stringent conditions suitable for finding related sequences would be performing the hybridization at a melting temperature (Tm) of between −15° C. to −20° C.

C. Cloning of the desired DNA sequences

Once the DNA encoding the desired sequences has been located, sufficient quantity of the gene must be generated to facilitate subsequent recombinant manipulations. Although the sequences can be directly amplified by PCR, they are most commonly replicated in an intermediate bacterial host. Most commonly in a bacteria of the genera Escherichia, Bacillus and Streptomyces. Cloning for amplification of intermediate vectors is most preferred in *E. coli* because that organism is easy to culture and more fully understood than other species of prokaryotes. The Sambrook manual contains methodology sufficient to conduct all subsequently described clonings in *E. coli*. Strain HB101 is a useful strain which is typically grown on Luria broth (LB) with glucose, Difco's Antibiotic Medium #2 and M9 medium supplemented with glucose and acid-hydrolyaed casein amino acids. Strains with resistance to antibiotics are maintained at the drug concentrations described in Sambrook.

Transformations are performed according to the method described by Morrison, D.A. (1977), *J. Bacteriol.*, 132:349–351; or by Clark-Curtiss, J. E. and Curtiss, R., 1983, in *Methods in Enzymology*, 101:347–362, Wu, R., Grossman, L. and Moldave, K., eds., Academic Press, New York. Representative vectors include pBR322 and the pUC series which are available from commercial sources.

D. Plant expression vectors

The desired expression vector comprises a expression cassette designed for operation in plants with companion sequences upstream and downstream from the expression cassette. The companion sequences will be of plasmid or viral origin and provide necessary characteristics to the vector to permit the vectors to move DNA from bacteria to the desired plant host.

The basic bacterial/plant vector construct will preferably provide a broad host range prokaryote replication origin; a prokaryote selectable marker; and, for Agrobacterium transformations, T DNA sequences for Agrobacterium-mediated transfer to plant chromosomes. Where the heterologous gene is not readily amenable to detection, the construct will preferably also have a selectable marker gene suitable for determining if a plant cell has been transformed. A general review of suitable markers for the members of the grass family is found in Wilmink and Dons, 1993, *Plant Mol. Biol. Reptr*, 11(2):165–185.

Sequences suitable for permitting integration of the heterologous sequence into the plant genome are also recommended. These might include transposon sequences and the like for homologous recombination as well as Ti sequences which permit random insertion of a heterologous expression cassette into a plant genome.

Suitable prokaryote selectable markers include resistance toward antibiotics such as ampicillin or tetracycline. Other DNA sequences encoding additional functions may also be present in the vector, as is known in the art.

The constructs of the subject invention will include the expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector. These elements are discussed in detail below.

i. Heterologous coding sequences.

The heterologous coding sequence may be for any protein of interest, either prokaryotic or eukaryotic, particularly eukaryotic. For the most part, the proteins of commercial interest will be mammalian proteins. The gene providing the desired product will particularly be those genes associated with large volume products. Therefore, products of particular interest include but are not limited to enzymes, such as chymosin, proteases, polymerases, saccharidases, dehydrogenases, nucleases, oxido reductases such as fungal peroxidases and laccases, xylanases, phytase, cellulase, hemicellulase, and lipase. More specifically, the invention can be used to produce enzymes such as those used in detergents, rennin, horse radish peroxidase, amylases from other plants, soil remediation enzymes.

Other proteins of interest, will for the most part be mammalian proteins, and will include blood proteins, such as serum albumin, Factor VII, Factor VIIIc, Factor VIIIvW, Factor IX, Factor X, tissue plasminogen factor, Protein C, von Willebrand factor, antithrombin III, erythropoietin, colony stimulating factors, such as G-, M-, GM-, cytokines, such as interleukins 1–11, integrins, addressins, selectins, homing receptors, surface membrane proteins, such as surface membrane protein receptors, T cell receptor units, immunoglobulins, soluble major histocompatibility complex antigens, structural proteins, such as collagen, fibroin, elastin, tubulin, actin, and myosin, growth factor receptors, growth factors, growth hormone, cell cycle proteins, vaccines, fibrinogen, thrombin, cytokines, hyaluronic acid and antibodies.

While for the most part, the product will be a peptidic product, genes may be introduced which may serve to modify non-peptidic products produced by the cells. These proteins, fragments thereof, usually of at least about 30 amino acids, fused combinations, mutants, and synthetic proteins, whether the proteins may be synthetic in whole or in part, so far as their sequence in relation to a natural protein, may be produced.

ii. Signal sequences.

The sequence encoding the protein of interest will encode a signal peptide which allows processing and translocation of the protein, as appropriate, and will usually lack any sequence which might result in the binding of the desired protein to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein. Table three provides a list of known signal sequences from wheat, barley and rice.

Table 3. Signal peptides of α-amylase genes

B-, barley α-amylase genes. W-, wheat α-amylase genes; #, signal peptide cleavage site determined by protein sequencing; *, predicted signal peptide cleavage site; /, intron splice site; ".", space inserted to maximize the alignment.

| Genes | References |
|---|---|
| RAmy1A | Plant Molecular Biology. 14:655–668 (1990). |
| RAmy1B | Nucleic Acids Research. 18:7007–7014 (1990). |
| aAmy10-c | Gene. 122:247–253 (1992). |
| W-Amy1/13 | Mol. Gen. Genet. 209:33–40 (1987). |
| W-2128 | Gene. 55:353–356 (1987) |
| B-pM/C | Plant Molecular Biology. 3:407–418 (1984) and Journal of Biological Chemistry. 260:3731–3738 (1985) |
| B-gKAmy141 | Plant Molecular Biology. 9:3–17 (1987). |
| RAmy2A | Gene. 111:223–228 (1992). |
| W-Amy2/54 | Mol. Gen. Genet. 209:33–40 (1987). |
| B-clone E | Plant Molecular Biology. 3:407–418 (1984) and J. of Biological Chemistry. 260:3731–3738 (1985). |
| B-gKAmy155 Plant | Plant Molecular Biology. 3:407–418 (1984) and Molecular Biology. 9:3–17 (1987). |
| B-Amy32b | Plant Molecular Biology. 3:407–418 (1984) and Nucleic Acids Research. 15:2515–2535 (1987). |
| RAmy3A | Plant Molecular Biology. 16:579–591 (1991) |
| RAmy3B | Plant Molecular Biology. 16:579–591 (1991) |
| RAmy3C | Plant Molecular Biology. 16:579–591 (1991) |

-continued

| Genes | References |
|---|---|
| RAmy3D | Nucleic Acids Research. 18:7007–7014 (1990). |
| RAmy3E | Nucleic Acids Research. 18:7007–7014 (1990). |
| W-Amy3/33 | Mol. Gen. Genet. 209:33–40 (1987). |
| Taka-amylase | Molecular Microbiology. 3:3–14 (1989). |

Those of skill can routinely identify new signal peptides. Plant signal peptides typically have a tripartite structure, with positively-charged amino acids at the N-terminal end, followed by a hydrophobic region and then the cleavage site within a region of reduced hydrophobicity. The conservation of this mechanism is demonstrated by the fact that cereal α-amylase signal peptides are recognized and cleaved in foreign hosts such as E. coli and S. cerevisiae.

The flexibility of this mechanism is reflected in the wide range of protein sequences which can serve as signal peptides. Thus, the ability of a sequence to function as a signal peptide may not be evident from casual inspection of the amino acid sequence. Methods designed to predict signal peptide cleavage sites identify the correct site for only about 75% of the sequences analyzed. (See Heijne Gv: Cleavage-site motifs in protein targeting sequences. In: J. K. Setlow (eds) Genetic Engineering, Vol. 14. Plenum Press, New York (1992)). Although, sequence homology is not always present in the signal peptides, hydrophilicity plots demonstrate that the signal peptides of these genes are relatively hydrophobic.

iii. Promoters

Promoters to direct m-RNA transcription should operate effectively in plant hosts. One such promoter is the nos promoter from native Ti plasmids, Herrera-Estrella et al., Nature 303:209–213, 1983. Others include the 35S and 19S promoters of cauliflower mosaic virus, Odell et al., Nature 313:810–812, 1985, and the 2' promoter, Velten, et al., EMBO J. 3, 2723–2730, 1984.

Conveniently, the transcription initiation region or promoter may be the transcription initiation region of the gene whose expression is to be inhibited, the same transcription initiation region for the gene encoding the desired product, or other convenient transcription initiation region.

The preferred transcriptional initiation or promoter region will be chosen so as to be relatively silent, except during seed germination. Desirably, the expression level in the seed cells should be at least about 20 times the expression level in other plant tissue during the growth of the plant. This can be achieved in various ways, by using the 5'-non-coding region associated with a protein which is produced solely or substantially solely during seed germination or by using the regulatory portion of such a transcriptional initiation region in conjunction with a different RNA polymerase binding region. In referring to a substantial absence of expression at other times than seed germination is intended that expression be very low or non-existent. That is, desirably the expression of the protein of interest should be very low so as not to affect the growth of the plant, nor to expend significant plant resources, so as to diminish the vigor of the plant growth, and depending on the protein of interest, to allow for the plant and mash to be used for its intended purpose.

A number of proteins are specifically encoded and secreted across either the aleurone or scutellum during seed germination and seed elongation. Some examples of secreted plant enzymes induced by gibberellic acid include: α-amylase, protease, ribonuclease, β-glucanase, esterase, acid phosphatases (such as p-nitrophenyl, phosphatase, ATPase, phytase, naphthol AS-B1 phosphatase, GTPase), pentosanase, endoxylanase, xylopyranosidase, arabinofuranosidase, glucosidase, and peroxidase.

One of skill will recognize that the list of promoter/signal sequence combinations are virtually limitless. Because many of the useful sequences are evolutionarily related, one can take advantage of conserved sequences to identify new promoters and signal sequences is included in this invention. The use of standard nucleic acid hybridization technology including traditional cross-hybridization experiments under varying solution stringencies using previously identified promoters and signal sequences to probe libraries of other grass plants. For example the barley promoter for HV18 (Seq ID No. 1) was identified using the rice RAmy1A as probe. Polymerase chain reaction technology [PCR] can also be used to amplify unknown promoter using PCR primers which are able to bind to conserved regions of a promoter or signal sequence. Examples of conserved sequences in the rice amylase promoter regions are provided in Table 2 below. The sequences for the rice promoters were reported in Huang N. et al. 1990, Nucl. Acids Res. 18:7007–7014 (1990) and the taka promoter from Aspergillus oryzae was reported in Wirsel, 1989, Molecular Microbiology, 3:3–14.

TABLE 2

Conserved sequences in the RAmy3D, RAmy3E and Taka-amylase promoters.
The "+" symbols indicate positions at which the Ramy3D and Ramy3E sequences are identical.

| | | |
|---|---|---|
| 31 bp RAmy3D | GAGACCGGGCCCCGACGCGGCCGACGCGGCG <br> ++++ + ++ +++ + ++ ++ +++++++ | SEQ ID No 3 |
| 31 bp RAmy3E | GAGAGCTCGCGCCGCCTCGATCGGCGCGGCG | SEQ ID No 4 |
| 11 bp RAmy3D | TTCCGGCTTGC <br> ++ ++++++++ | SEQ ID No 5 |
| 11 bp RAmy3E | TTGCGGCTTGC | SEQ ID No 6 |
| Taka-amylase | CGGCCCGTCGGC | SEQ ID No 7 |

The situation in rice is demonstrative. In rice, the α-amylase isozymes are encoded by a family of nine genes (Table 1). They are referred to as RAmy1A,-1B, 1C, 2A,3A, 3B,3C, 3D and 3E. The Rice α-Amylase genes are classified into three subfamilies (RAmy1, RAmy2, and RAmy3) [See Huang et al., 1992, Proc. Natl. Acad. Sci. USA. 89:7526–7530 and Huang N et al. 1990, Plant Molecular Biology, 14:655–668) based on DNA sequence similarities to α-amylase gene subfamilies in other cereal species. Eight members of the α-amylase gene family in rice have been isolated and characterized. A partial cDNA sequence, presumably corresponding to RAmy1C, has been reported in Yu S-M et al. 1992, Gene. 122:247–253. The α-amylase genes have been mapped to five different chromosomes in rice.

TABLE 1

Alpha-amylase gene expression in rice tissues The nine α-amylase genes represent all members of the gene family found in rice cv. IR36.

| gene name | germinated seedlings | root | leaf | developing seeds | cultured cells |
|---|---|---|---|---|---|
| All Genes | 100[a] | 1 | 3 | 4 | 65 |
| RAmy1A | ++++[b] | ++++ | ++++ | +++ | ++ |
| RAmy1B | – | – | – | – | + |
| RAmy1C | –[c] | NA[d] | NA | NA | NA |
| RAmy2A | + | + | + | + | + |
| RAmy3A | + | – | – | – | ++ |
| RAmy3B | ++ | NA | NA | NA | NA |
| RAmy3C | ++ | NA | NA | NA | NA |
| RAmy3D | ++ | ++ | ++ | – | ++++ |
| RAmy3E | +++ | +++ | +++ | ++++ | +++ |

[a]Relative mRNA levels for all α-amylase genes are normalized to the level of expression observed in germinated seedlings by Northern blot hybridization.
[b]Relative levels of mRNA for each gene as estimated from Northern blot hybridization or RNA-PCR experiments. The amount of PCR product is indicated from the highest (++++) to the lowest (+). Minus signs (–) indicate that no product was observed in the RNA-PCR reaction.
[c]Lack of expression based on restriction digest of RNA-PCR products.
[d]NA = Not Available Desirably, the preferred promoter/signal sequence combinations include 1A, 3D and 3E, where expression is at a high level during germination. The 5'-non-coding region of 3E is characterized by a region conserved with 3D, which is a GC-rich sequence of 31 bases and contains two CGGC repeats. There is also an 11 base sequence which is conserved which contains a single copy of the CGGC sequence. The 3D and 3E α-amylase genes are subject to suppression of expression by sugars, particularly sucrose, glucose, fructose, and maltose. Thus, during cell fermentation, premature expression of the desired product can be avoided by employing a sugar, particularly, sucrose, in the growth medium. Thus, sucrose may be used as a carbon source by the cells and, when the sucrose is exhausted, expression of the desired proteins will be initiated. Others transcriptional initiation regulatory regions which may be employed include those that are induced by sugar such as sucrose synthase.

One may employ complex transcriptional initiation regions by employing the regulatory portion of one transcriptional initiation region with the RNA polymerase binding region of a different gene. In this way, one may enjoy the regulation of expression, while providing for a high level of expression.

A preferred embodiment uses a promoter that is regulated during germination. For example the hormones abscisic acid (ABA) and gibberellic acid (GA) play important regulatory roles in control of α-amylase gene expression in cereal seeds. ABA, which is synthesized during grain filling, acts as a negative regulator of transcription for α-amylase and many other genes. ABA levels drop in the mature desiccated grain, thus relieving the inhibition of α-amylase and other genes required for germination. Obviously up-regulation is desired for over expression of heterologous proteins and GA mediated promoters are a desired embodiment. The prevailing model for GA regulation during cereal seedling development involves the diffusion of GA from the embryo to the aleurone layer. GA then induces the synthesis of hydrolytic enzymes such as α-amylase. In rice, GA stimulates α-amylase gene expression in aleurone tissues. But not all α-amylase promoters are induced by GA and not all are inducible when present in undifferentiated cells such as those used in culture or when removed from the intact seed. For example RAmy3D and RAmy3E in rice callus and cultured cells are unaffected by GA. No significant change in levels of RAmy3D and RAmy3E expression was detected in rice callus treated with GA and there are reports that callus treated with paclobutrazol, an inhibitor of gibberellin biosynthesis, produced the same amount of α-amylase protein as untreated callus. Finally, callus cultures derived from seeds of the GA-deficient dwarf mutant, cv. Tan-ginbozu, produced the same levels of α-amylase gene expression with or without exogenous GA treatment. This suggests that Ramy3D and Ramy3E gene expression in the scutellum and in cultured cells is independent of GA regulation.

The GA independent promoters appear to be missing a short sequence that is present in GA inducible promoters. DNA sequence comparisons have identified four short, conserved sequences in the cereal α-amylase promoters. The TATA Box (CTATAAATAG) is the binding site required for RNA polymerase II to initiate transcription. The Pyrimidine Box (YCTTTTY) and Box I (TATCCAT) may be involved in the developmental regulation of the genes in the scutellum and aleurone. The GARE Box (GA-Responsive Element) (TAACRRA) is required for GA-induction and ABA-repression of α-amylase gene expression. The GARE Box (GA-Responsive Element) in the RAmy1A gene (genomic clone 10Sg2) is located at base −143 relative to the transcription start site. Expression of the RAmy1A gene (cDNA clone pOS103) is stimulated 50–100 fold by exogenous GA. The absence of GARE Box sequences in the promoters of the rice RAmy3D and RAmy3E genes is consistent with the GA-independent expression of these genes as discussed above.

Alternatively the agent inducing expression can be a metabolite which is either a sugar or phosphorylated sugar. For example, RAmy3D gene expression is metabolically regulated in rice embryo tissues. Evidence for this is based on studies in which seeds were moistened to initiate seedling development and harvested after 0 to 48 hours of incubation. Embryos dissected out of these seeds had low levels of expression for RAmy3D. This pattern of expression was reversed if embryos were first removed from the seed at time zero and incubated in water for 0 to 48 hours Under these conditions, RAmy3D expression increased to five times the level observed in the intact rice seed. Addition of sugar to the incubation medium used for the isolated embryos restored normal expression of the RAmy3D gene (see examples). A number of sugars, including sucrose, glucose, fructose and maltose, were able to repress RAmy3D gene expression in isolated embryos (Karrer and Rodriguez, 1992, *The Plant Journal*, 2:517–523).

In rice cell suspension cultures, α-amylase enzyme activity increases after the depletion of sucrose from the medium. This increase is consistent with the pattern of α-amylase mRNA accumulation, which also increases dramatically after the culture medium is depleted of sugar. Cells transferred to sugar-free medium begin to produce elevated levels of total α-amylase mRNA within four hours. (See Yu S-M, et al., 1991, *J Biol. Chem.* 266:21131–21137 (1991). Dot blot hybridization and gene-specific probes have been used to demonstrate that sugar controls the expression of both RAmy3D and RAmy3E in cultured cells. Cells were subcultured into medium with 1%, 3%, 6% or 12% sucrose. RNA isolated from cells cultured for five days showed that RAmy3D and RAmy3E expression was repressed at the higher sugar concentrations. Expression of both of these genes was induced in the cells cultured in 1% sucrose, presumably after sugar was depleted from the medium by cell growth. Expression of the RAmy1A and RAmy3A genes was unaffected by these treatments. Thus, expression of the RAmy3D and RAmy3E genes is metabolically regulated by the concentration of sugar in the culture medium.

To confirm that this regulation is acting at the level of transcription, the RAmy3D promoter was linked by us to the GUS reporter gene. The amount of GUS enzyme activity produced by the cells provides a convenient measure of the expression of the engineered RAmy3D promoter. The RAmy3D promoter/GUS gene construct was co-electroporated into protoplasts with another plasmid containing the gene for hygromycin-resistance. Southern blot hybridization showed that hygromycin-resistant cell lines contained the RAmy3D/GUS gene construct. GUS activity was reduced in transformed cell lines grown at elevated sucrose concentrations (see examples). GUS activity increased starting eight hours after the cells were transferred to sugar-free medium. These data demonstrate that the GUS reporter gene is being regulated by the RAmy3D promoter in cell culture just as the endogenous RAmy3D gene is regulated in the rice seed.

The promoters of the RAmy3D and RAmy3E genes have little sequence similarity, but there are two conserved sequences in their promoters that may be involved in the metabolic regulation of these genes. A GC-rich sequence of 31 bases in RAmy3D (Table 2) contains two CGGC repeats (underlined). This tandem repeat structure within the 31 base sequence is similar to the DNA binding sites for Sp1, a mammalian transcription regulatory protein. An eleven-base sequence (Table 2), which is conserved in both the RAmy3D and the RAmy3E promoter, contains a single copy of the CGGC sequence. A tandem duplication of the CGGC sequence is also found in the promoters of the Taka-amylase genes of *Aspergillus oryzae*. These CGGC sequences are found in the 87 base region of the Taka-amylase promoters (from position −377 to −290) that has been implicated in the metabolic regulation of these genes.

iv. Transcription and translation terminators

The expression cassette is terminated with a transcriptional termination region. The transcriptional termination region may be normally associated with the transcriptional initiation region or from a different gene. The transcriptional termination region may be selected, particularly for stability of the mRNA to enhance expression. Illustrative transcriptional termination regions include the NOS terminator from Agrobacterium Ti plasmid and the rice α-amylase terminator.

Polyadenylation tails, Alber and Kawasaki, 1982, *Mol. and Appl. Genet.* 1:419–434 are also commonly added to the expression cassette to optimize high levels of transcription and proper transcription termination, respectively. Polyadenylation sequences include but are not limited to the Agrobacterium octopine synthetase signal, Gielen et al., *EMBO J.* 3:835–846, 1984 or the nopaline synthase of the same species Depicker et al., *Mol. Appl. Genet.* 1:561–573, 1982.

Since the ultimate expression of the desired gene product will be in a eucaryotic cell (e.g.,a member of the grass family), it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95–105, 1985.

E. Transformation of plant cells i. Direct Transformation

The vector can be microinjected directly into plant cells by use of micropipettes to mechanically transfer the recombinant DNA. Crossway, *Mol. Gen. Genet*, 202:179–185, 1985. The genetic material may also be transferred into the plant c/ell by using polyethylene glycol, Krens, et al., *Nature,* 296, 72–74, 1982.

Another method of introduction of nucleic acid segments is high velocity ballistic penetration by small particles with the nucleic acid either within the matrix of small beads or particles, or on the surface, Klein, et al., *Nature,* 327, 70–73, 1987 and Knudsen and Muller, 1991, *Planta,* 185:330–336 teaching particle bombardment of barley endosperm to create transgenic barley.

Yet another method of introduction would be fusion of protoplasts with other entities, either minicells, cells, lysosomes or other fusible lipid-surfaced bodies, Fraley, et al., *Proc. Natl. Acad. Sci. USA,* 79, 1859–1863, 1982.

The vector may also be introduced into the plant cells by electroporation. (Fromm et al., *Pro. Natl Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

ii. Vectored Transformation

A common vector method of introducing the vector into plant cells is to infect a plant cell with *Agrobacterium tumefaciens* previously transformed with the gene. Under appropriate conditions known in the art, the transformed plant cells are grown to form shoots or roots, and develop further into plants.

Agrobacterium is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes.

Heterologous genetic sequences such as the chimeric aadA gene can be introduced into appropriate plant cells, by means of the Ti plasmid of *Agrobacterium tumefaciens.* The Ti plasmid is transmitted to plant cells on infection by *Agrobacterium tumefaciens,* and is stably integrated into the plant genome. J. Schell, *Science* 237: 1176–1183, 1987.

Ti plasmids contain two regions essential for the production of transformed cells. One of these, named transferred DNA (T-DNA), is transferred to plant nuclei and induces tumor formation. The other, termed virulence region, is essential for the transfer of this T-DNA but is not itself transferred. The transferred DNA region, which transfers to the plant genome, can be increased in size by the insertion of the gene encoding group 3 LEA proteins without its ability to be transferred being affected. A modified Ti plasmid, in which the tumor-causing genes have been deleted, can be used as a vector for the transfer of the gene constructs of this invention into an appropriate plant cell.

Construction of recombinant Ti plasmids in general follows methods typically used with the more common bacterial vectors such as pBR322. Additional use can be made of accessory genetic elements sometimes found with the native plasmids and sometimes constructed from foreign sequences. These may include but are not limited to "shuttle vectors", Ruvkun and Ausubel, 1981, *Nature*298:85–88, promoters, Lawton et al., 1987, *Plant Mol. Biol.* 9:315–324 and structural genes for antibiotic resistance as a selection factor, Fraley et al., *Proc. Nat. Acad. Sci.* 80:4803–4807, 1983.

Species which are a natural plant host for Agrobacterium may be transformable in vitro. Monocotyledonous plants, and in particular, cereals and grasses, are not natural hosts to Agrobacterium. Attempts to transform them using Agrobacterium have been unsuccessful until recently. Hooykas-Van Slogteren et al., *Nature* 311:763–764, 1984. There is growing evidence now that certain monocots can be transformed by Agrobacterium. Using novel experimental approaches that have now become available, cereal and grass species may now be transformed.

F. Plant Regeneration

After determination of the presence and expression of the desired gene products, whole plant regeneration is desired. Plant regeneration from cultured protoplasts is described in Evans et al., *Handbook of Plant Cell Cultures, Vol.* 1: (MacMillan Publishing Co. New York, 1983); and Vasil I. R. (ed.), *Cell Culture and Somatic Cell Genetics of Plants,* Acad. Press, Orlando, Vol. I, 1984, and Vol. III, 1986.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus,. Lycopersion, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum, and Datura.

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, are selfed and non-segregating, homozygous transgenic plants are identified. The inbred plant produces seed containing the gene for the LEA protein product. These seeds can be grown to produce plants that exhibit the desired dwarfing characteristic.

The inbreds according to this invention can be used to develop hybrids or novel varieties embodying the desired traits. Such plants would be developed using traditional selection type breeding.

G. Antisense applications

In addition to the above indicated genes, one may also have constructs which provide for inactivation of endogenously expressed genes. Of particular interest will be the inactivation of genes which are expressed during germination and seedling elongation. These genes may include one or more of the amylases, RAmy3B, RAmy3C, RAmy3E.

Inactivation may be achieved in a number of ways. The most convenient will be the use of an anti-sense sequence, where the anti-sense sequence may be complementary to any portion of the mRNA, including both the non-coding and coding regions. Normally, the anti-sense sequence will be at least about 30 nt, more usually at least about 50 nt, and may be up to or greater than the sequence of the MRNA to which the anti-sense sequence is complementary. Desirably, the 3'-terminal sequence of the anti-sense sequence will be selected to provide for mRNA stability, there being a number of sequences which are known to destabilize the MRNA which can be avoided.

The transcription initiation region for the anti-sense sequence may be constitutive or inducible. A relatively strong promoter may be employed, such as the 35S CMV promotor, the RUBSICO promoter, beta-conglycinin promoter etc. Preferably, the transcription initiation region will be inducible so as to be induced during the malting process. To enhance the transcription of the anti-sense sequence, one may use various enhancers associated with other promoters to increase the rate of transcription of the anti-sense sequence. It is not necessary that all expression of one or more proteins naturally produced during malting is inhibited, it being sufficient that there be at least about a 10%, preferably at least about a 25% reduction in expression, so as to increase the proportion of the desired protein in the malting product. Enhancers which find use include the 35S CMV enhancer, and the introns of the alcohol dehydrogenase gene of maize.

H. Malting

The malting process is a multistep process. The first step is steeping. During steeping seed is immersed in or sprayed with water to increase the moisture content of the seed to between 35–45%. This initiates germination. Steeping typically takes place in a steep tank which is typically fitted with a conical end to allow the seed to flow freely out. The addition of compressed air to oxygenate the steeping process is an option. The temperature is controlled at approximately 22° C. depending on the seed.

After steeping, the seed is transferred to germination compartments. The seed is either wet or dry transferred. The germination bin contains air saturated with water and is under controlled temperature and air flows. The typical temperatures are between 12°–25° C. and germination is permitted to continue for from 3 to 7 days.

Where the heterologous protein is operably linked to an inducible promoter requiring a metabolite such as sugar or plant hormone, this metabolite is added, removed or depleted from the steeping water medium and/or is added to the water saturated air used during germination. The seed will absorb the aqueous medium and begin to germinate expressing the heterologous protein. The medium may then be withdrawn and the malting begun, by maintaining the seeds in a moist temperature controlled aerated environment. In this way, the seeds may begin growth prior to expression, so that the expressed product will be less likely to be partially degraded or denatured during the process. Other components included in the imbibition medium may be plant hormones, such as gibberellic acid, generally in an amount from about 2.5 to 100 µm.

Where the promoter is induced by sugar, glucose or sucrose can be added to the imbibition media during steeping or during germination. The sugar concentration may range up to about 12 weight percent of the medium.

More specifically, the temperature during the imbibition or steeping phase will be maintained in the range of about 15°–25° C., while the temperature during the germination will usually be about 20° C. The time for the imbibition will usually be from about 2 to 4 days, while the germination time will usually be an additional 2 to 10 days, more usually 3 to 7 days. Usually, the time for the malting does not exceed about ten days. The period for the malting can be reduced by using plant hormones during the imbibition, particularly gibberellic acid.

To achieve maximum production of recombinant protein from malting, the malting procedure will be modified to accommodate de-hulled and de-embryonated seeds. The hulls and embryos are dehulled and de-embryonated using standard means which include rollers, other mechanical means of breaking the intact embryos free of hull and endosperm. Screening is typically used to separate the embryos from unwanted seed debris. Isolated transgenic embryos are germinated in steeping water containing $CaCl_2$ (approx 10 mM). In the absence of sugars from the endosperm, there is expected to be a 5 to 10 fold increase in RAmy3D promoter activity and thus expression of the heterologous protein. Alternatively when embryoless-half seeds are incubated in 10mM $CaCl_2$ and 5 µm gibberellic acid, there is a 50 fold increase in RAmy1A promoter activity.

In this system, recombinant proteins under the control of RAmy1A (or HV18) and RAmy3D promoters will be secreted into the medium through the bottom of a specialized malting bin or steep tank. The embryos and embryoless-half seeds will then be mechanically disrupted to release any secreted protein between cells and tissues. The mixture will be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

An optional step is kilning the germinated seed. Kilning is a low temperature drying procedure that reduces moisture concentration to 4–6%. Temperatures during kilning are between 40°–85° C. Typically the lower temperatures of less than 60° C. are used until the seed have a moisture content of between about 10 and 20%. Final drying is at higher temperatures of above 60° C.

The mash may then be processed by mechanical disruption of the seeds and bringing the total protein into solution. The cellular debris may then be separated by any convenient means, such as settling, centrifugation, filtration, or the like. The supernatant or filtrate will normally include from 1 to 40 weight percent of the desired product of total protein in the medium, preferably at least about 30 weight percent. Where the desired product is not water soluble, one may need to extract the desired product with a convenient solvent or use another process which allows for solubilization and/or extraction of the product without loss of the desired activity of the product or which allows for renaturation.

After isolation of the protein from the aqueous medium, one may then purify the product in accordance with conventional ways. Since the product will be a substantial portion of the total protein present in the mixture, frequently being present in the greatest percentage of any individual protein, purification is greatly simplified. Furthermore, contaminants in the product after purification are not likely to be of physiological concern for many of the applications of the products, including therapeutic applications.

I. Cell culture

The vectors of this invention can be used to facilitate the expression and secretion of heterologous protein into cell culture. The plant cells are placed and maintained into suspension culture and induced through the variety of inducers described above to produce high levels of the desired heterologous protein. The protein is then isolated using conventional technology. Because the purifications are dramatically varied for individual proteins, it is sufficient to indicate that the initial purification process will typically follow the purification process of the native protein from its host. Because the growth media of the suspension culture is markedly more simple and free of host contaminants, the procedures may be appropriately modified and simplified by those of skill.

It is evident from the above results, that one can engineer plant cells and use the cells to propagate plants. One can modify the plant cells to provide for expression constructs which allow for controlled expression of the coding sequence in the construct to provide the expression product as the major product. By providing for malting, seeds can be germinated under conditions where a desired product can be produced in the germinated seeds to provide for a high proportion of the total protein in the malting mash being the desired protein. By breaking the cells, separating the cellular debris from the protein, and isolating the supernatant from the mash, the protein may be easily isolated and purified, being a major component of the total protein in the medium. As distinct from other methods of producing proteins, the subject method provides for high levels of economic production of proteins in a crude form which can be easily purified. The system lacks the potential for the production of endo and exotoxins, which is of concern with prokaryotes. The system allows for storage under ambient conditions without significant loss of seed viability or product loss. The product can be produced on demand. In this way, proteins can be produced in accordance with need, where the source of the protein can be conveniently and safely stored.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

Example 1

Expression of β-glucuronidase under the control of the α amylase promoter in rice cell culture.
Materials and Methods
Initiation of callus and suspension cultures Rice seeds (*Oryza sativa* L. cv. M202) were provided by Dr. M. Brandon (California Rice Experimental Station). Seeds were dehulled, washed three times with water, rinsed in 70% ethanol for 20 sec and then surface-sterilized in 1% sodium hypochlorite with a few drops of Tween 20 under vacuum for 20 min. Sterilized seeds were washed three times with sterile distilled water. Seven seeds were placed in 15 cm petri dishes containing LS medium with 2 mg/1,2,4-D and 30 sucrose. The seeds were incubated in the dark at 28° C. and checked periodically to monitor the growth of callus. Callus formation from scutellum tissue and/or embryo was visible after 5 days. After 30 to 40 days, clumps of friable calli, about 1 cm in diameter, were saved and the remaining tissue was discarded.

To initiate a suspension culture, friable calli were gently agitated in a petri dish with liquid AA medium as described by Thompson JA, Abdullah R and Cocking EC, Protoplast culture of rice (*Oryza sativa* L.) using media solidified with agarose. *Plant Sci.* 47:123–133 (1986). to reduce the calli to small clusters of cells. Cell clusters from about 20–30 clumps of calli were then transferred to a 125 ml Erlenmyer flask and the liquid was replaced with 25 ml of fresh AA medium. The flasks were incubated in the dark on a rotary platform shaker at 110 rpm and 28° C. The primary culture was sub-cultured every 4 to 5 days with repeated screening for small cell clusters. This was accomplished by passing the culture sequentially through nylon filters of 1000 µm and 500 µm pore size. After two months of subculture, a finely divided and rapidly growing suspension culture was obtained. This culture was subsequently maintained by weekly subculture in AA medium containing 3% sucrose.
Construction of the RAmy3D/GUS gene fusion The RAmy3D promoter/GUS gene fusion shown in FIG. 4 was constructed in three steps. First, a 1.5 kb SalI fragment containing the promoter and part of the coding region from rice genomic clone λOSg1A as described by Huang et al., 1990a, *Nucleic Acid Res.*, 18:7007–7014 was subcloned into pBluescript KS– to produce the plasmid p1AS1.5. The AluI fragment from p1AS1.5 containing 876 bp of promoter and 66 bp of 5' untranslated region was subcloned into the EcoRV site of pbluescript KS+ to form p1Alu. Second, a plasmid containing a promoterless GUS cassette was constructed by subcloning the HindIII/EcoRI GUS cassette from pBI101 (Jefferson RA, 1987, Assaying chimeric genes in plants: the GUS gene fusion system. *Plant Mol. Biol. Reporter*, 5:387–405) into pUC19 to form pBI201. A pUC19 polylinker in front of the GUS coding region provides convenient cloning sites for inserting promoter fragments. Third, the RAmy3D promoter fragment was inserted into the promoterless GUS plasmid to produce the plasmid p3DG. The XbaI/AluI (in HindIII site) promoter fragment from p1Alu was ligated into XbaI/SmaI digested pBI201. The final 11 bp of RAmy3D 5' untranslated region was substituted by 21 bp from the polylinker resulting in the 5.83 kb plasmid, p3DG. The junction between the RAmy3D promoter and the 5' end of the GUS gene was confirmed by DNA sequencing. DNA restriction digest, DNA gel electrophoresis, ligation, transformation, plasmid DNA isolation and DNA sequencing followed standard procedures (Sambrook, et al., *Molecular Cloning—A Laboratory Manual*, Cold Spring Harbor Laboratory, Cold Spring Harbor, N.Y. 1989.
Protoplast isolation and DNA transformation Three days after subculture, a 60 ml of rice suspension culture was given a ten minute, 45° C. heat-treatment and transferred to two glass crystallizing-dishes. The AA medium was removed and the cells in each dish were mixed with the 20 ml of enzyme mixture (1% Cellulose RS, 1% Macerozyme R10 in CPW medium described by Thompson et al., 1986, *Plant Sci.* 47:123–133. The cell walls were digested at 28° C. for 15 hours while shaking at 45 rpm. After digestion, the protoplasts were screened through 150, 50 and 20 µm nylon filters, washed three times by centrifuging for 10 min at 80 g, and gently resuspended in 40 ml of CPW medium. Then the suspension was adjusted to 5 million protoplasts/ml.

Two and one-half million protoplasts in 0.5 ml volume were mixed with 5 µg of p3D2 DNA, 25 µg of calf thymus carrier DNA and 5 µg of pGL2 plasmid DNA carrying the CaMV 35S promoter/hph gene fusion encoding hygromycin-resistance as described by Shimamoto K, Terada R, Izawa T and Fujimoto H: Fertile transgenic rice plants regenerated from transformed protoplasts *Nature* 338:274–276 (1989), transferred to a cuvette, placed on ice for ten min, then electroporated with a Gene Pulser electroporator (Bio-Rad) (300 volt/cm, 560 mF and 600 Ohms). After being kept on ice for an additional 10 min, the protoplasts were mixed with 0.5 ml of 4× KPR medium (Thompson et al. Supra 1986) and 1 ml of melted 2.4% Sea Plaque low gelling agarose, plated in Petri dishes and incubated at 28° C. in the dark.

Ten days after plating, the agarose in each Petri dish was separated into four pieces and transferred into a 6 cm Petri dishes containing 5 ml of liquid KPR medium. Four days later hygromycin was added to each dish to a final concentration of 50 mg/ml. Hygromycin-resistant colonies were picked and grown in liquid AA medium to form a number of cell lines. A sample from each cell line was then assayed for GUS activity by staining the cells with X-glu (Jefferson et al. supra 1987). Cell lines having GUS activity were retained. Uniform cell lines were obtained by two additional rounds of isolating cell single cell clusters coupled with selection for GUS expression. Integration of p3DG DNA into the rice genome was verified by Southern blot analysis.

RNA isolation and dot blot hybridization

Total RNA was isolated from cell suspension culture using a modification of the phenol/SDS procedure Ausubel F. M., Brent R, Kingston R. E., Moore D. D., Seidman J. G., Smith J. A. and Struhl K: Current Protocols in Molecular Biology. (1989). Approximately one gram of cultured rice cells were ground into a fine powder with sand and 5 ml of liquid nitrogen until all the liquid nitrogen evaporated. Then 2.5 ml of TLE buffer (0.2 M Tris pH. 8.2, 0.1 M LiCl, 5 mM EDTA, 20 mM sodium metabisulfite) was added and grinding continued until the sample was completely liquefied. At this point, 0.5 ml of 10% SDS, 2.5 ml of phenol and 2.5 ml of chloroform were added to the mortar sequentially and mixed well by grinding. The sample was centrifuged at 4000 g for 15 min and the aqueous phase removed and extracted with chloroform. Total RNA was precipitated by the addition of 1/3 volume of 8 M LiCl and the mixture was allowed to sit overnight at 4° C. The RNA was harvested by centrifugation at 16,000 g for 30 min at 4° C. and the RNA pellet was dissolved in 0.5 ml of double distilled water treated with diethylpyrocarbonate. The RNA was extracted once more with chloroform and then precipitated with ethanol. The RNA yield was approximately 500 µg from each gram (fresh weight) of cells.

The pre-hybridization and hybridization of α-amylase probe to the membrane under α-amylase group-specific conditions was as previously described by Huang N, Koizumi N, Reinl S and Rodriguez R. L.: Structural organization and differential expression of rice α-amylase genes *Nucleic Acids Res.* 18:7007–7014 (1990a) and Huang N, Sutliff T. D., Litts J. C. and Rodriguez R. L.: Classification and characterization of rice α-amylase multigene family. *Plant Mol. Biol.* 14:655–668 (1990b).

Four different rice α-amylase genes were used as probes. The RAmy1A probe, a 1.6 kb XbaI fragment from pOS103 described in O'Neill S. D., Kumagai M. H., Majumdar A, Huang N, Sutliff T. D. and Rodriguez R. L.: The α-amylase genes in *Oryza saliva*: characterization of CDNA clones and MRNA expression during seed germination. Mol. Gen. Genet. 221:235–244 (1990) cross hybridized with the closely related genes RAmy1B and RAmy3C under the stringency conditions used. The RAmy3D probe, a 1.6 kb XbaI fragment from pOS137 [O'Neill supra] was used under gene-specific conditions. The RAmy3A probe, a 3.5 kb EcoR1 fragment from λOS7D (Sutliff T. D., Huang N, Litts J. C. and Rodriguez R. L.: Characterization of an α-amylase multigene cluster in rice. *Plant Molecular Biology*. 16:579–591 (1991)) was used under highly stringent, gene-specific conditions. The RAmy3E probe, a 2 kb HindIII fragment including the two introns exons II and III, and the 3' end as described by Huang N, Koizumi N, Reinl S and Rodriguez RL: Structural organization and differential expression of rice α-amylase genes. *Nucleic Acids Res.* 18:7007–7014 (1990a).

DNA isolation and Southern blot hybridization

Total genomic DNA was isolated using a small scale CTAB procedure described by Rogers S. O. and Bendich A. J.: Extraction of DNA from milligram amounts of fresh, herbarium and mummified plant tissues. *Plant Mol. Biol.* 5:69–76 (1985) Southern blot analysis of transformed and untransformed cultured cells was the same as previously described in Huang N, Sutliff T. D., Litts J. C. and Rodriguez R. L.: Classification and characterization of rice α-amylase multigene amily. Plant Mol. Biol. 14:655–668 (1990b).

The DNA probes used were the HindIII/EcoRI fragment of pBI201 (Jefferson, Supra) for the GUS gene and pOS103 as described in O'Neill SD, Kumagai MH, Majumdar A, Huang N, Sutliff T. D. and Rodriguez R. L.: The α-amylase genes in *Oryza saliva*: characterization of CDNA clones and MRNA expression during seed germination. *Mol. Gen. Genet.* 221:235–244 (1990) for rice α-amylase gene RAmy1A.

Isolation of total protein and β-glucuronidase (GUS) activity assay

Total water soluble protein was isolated from suspension culture cells based on the procedure described by Jefferson supra. A 200 mg sample of suspension culture cells was ground in a mortar and pestle for one min in the presence of sand and 0.5 mi of GUS extraction buffer (Jefferson supra). The slurry was transferred to a 1.5 ml microfuge tube and the cell debris removed after 5 min of centrifugation at room temperature. The supernatant was saved as a crude extract of water soluble protein. The GUS activity was measured by the fluorometric assay procedure (Jefferson supra) The background level of GUS activity in control, untransformed cells was negligible.

GUS activity was also assayed in whole cultured cells by calorimetric methods (Jefferson supra). Fresh or frozen cultured cells were put in either a 1.5 ml tube, a 3.5 cm Petri dish or a microtiter plate. Five volumes of sterile X-glu solution were added to the cells. The reaction was incubated at 37° C. for 30 min. or longer.

RESULTS

Metabolic regulation of RAmy3D and RAmy3E in untransformed rice suspension cultures The above experiments allow for the determination of which rice α-amylase gene(s) is metabolically regulated in rice cell cultures. Total RNA was isolated from a cell culture sampled over a period of eight days. RNA dot blots were hybridized sequentially with four different α-amylase gene probes. The mRNA levels for the RAmy1A, RAmy1B and RAmy1C genes were low and did not change significantly during the eight day period. The level of RAmy3A mRNA was also low and showed little change during the culture cycle. The levels of RAmy3D and RAmy3E mRNA were low initially, but increased significantly after five days, reaching their peak levels at 8 and 6.5 days respectively. These results are consistent with previous studies which demonstrated that RAmy3D (Group 2) and RAmy3E (Group 5) mRNA were abundantly expressed in rice cell culture while the expression of RAmy1A/RAmy1B/RAmy1C (Group 1), RAmy2A (Group 4) and RAmy3A/RAmy3B/RAmy3C (Group 3) was either low or undetectable. Other workers have found moderate expression of RAmy1A and another gene in the Ramy1 subfamily, but only in 14 day old cell cultures.

The concentration of sugar in the rice cell suspension culture medium correlates with the amount of α-amylase enzyme produced by the cells. To investigate this effect at the gene level, suspension cultures, normally maintained in medium containing 3% sucrose, were subcultured into media with 1%, 3%, 6% or 12% sucrose. RNA was isolated from cells harvested at one day and at five days after subculture. RNA dot blots were hybridized with α-amylase gene probes. All cells harvested after one day had approximately the same levels of α-amylase gene expression, presumably because none of the cultures had yet depleted the sucrose from the medium. The mRNA levels for the RAmy3D and RAmy3E genes increased significantly after five days in the culture with 1% sucrose medium, showing induction of gene expression after the sugar was depleted from the medium. Cultures with higher initial sucrose concentrations still had only low levels of RAmy3D and RAmy3E gene expression after five days. The levels of RAmy1A, RAmy1B, RAmy1C and RAmy3A gene expression changed little in any of the cultures.

Sucrose concentrations in the culture medium were altered to test the effect on α-amylase gene repression. After four days of culture in medium with an initial sucrose concentration of 3%, cultures were subdivided and the sucrose concentration was increased to 6% and 12%. One of the cultures was washed and resuspended in sucrose-free medium (0%). Cultures were incubated for two more days and RNA was isolated for analysis by slot blot hybridization. RAmy1A, RAmy1B, RAmy1C and RAmy3A expression levels were consistently low in all subcultures. RAmy3D gene expression was significantly reduced in subcultures supplemented with 6% or 12% sucrose, relative to that of the sucrose-free subculture. RAmy3E gene expression remained high in all treatments. Thus, within two days after the addition of sucrose to the culture media, RAmy3D was highly repressed while RAmy3E expression was relatively unchanged. It is not clear to what extent these results are due to differential transcriptional control and/or differential mRNA stability.

Transformation of RAmy3D promoter/GUS into rice cell lines

Figure 2:
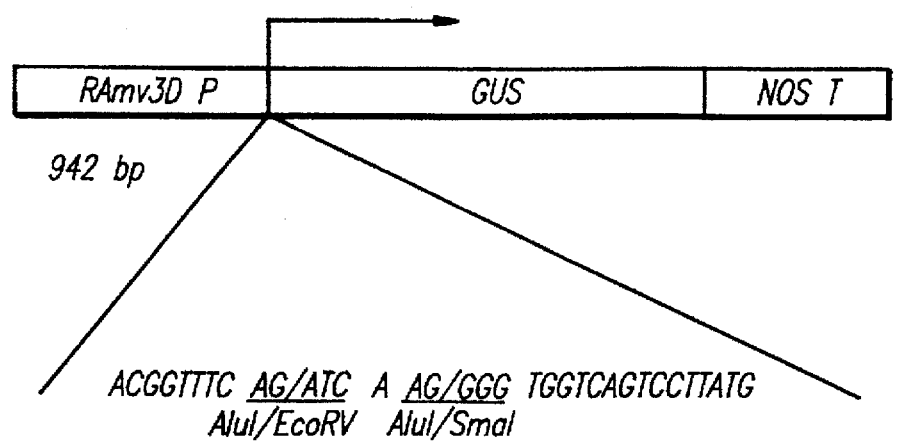
FIG. 2 is a depiction of the plasmid construction for producing transgenic seed with a RAmy3D promoter.

A RAmy3D promoter/GUS gene fusion was constructed and used to transform rice protoplasts. The plasmid p3DG contains 876 bp of RAmy3D 5' flanking region plus 66 bp of the 5' untranslated leader sequence linked to the GUS coding region (FIG. 2). Plasmid p3DG was introduced into rice protoplasts by co-electroporation with the plasmid pGL2 which carries the hygromycin-resistance gene. Protoplast-derived colonies were selected on hygromycin-containing medium and tested for co-transformation with the RAmy3D/GUS construct by staining a few cells from each colony for GUS activity. Two cycles of hygromycin-resistance selection and GUS activity screening were used to isolate the 3DG cell line.

Figure 3A:
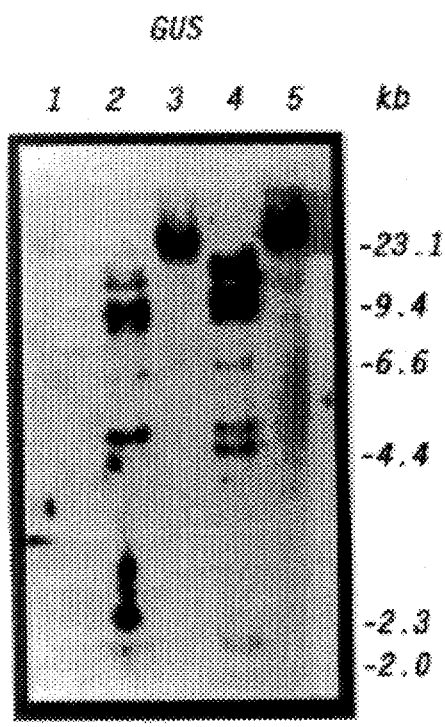
FIGS. 3A and 3B demonstrate the results of southern blot hybridization.
Figure 3B:
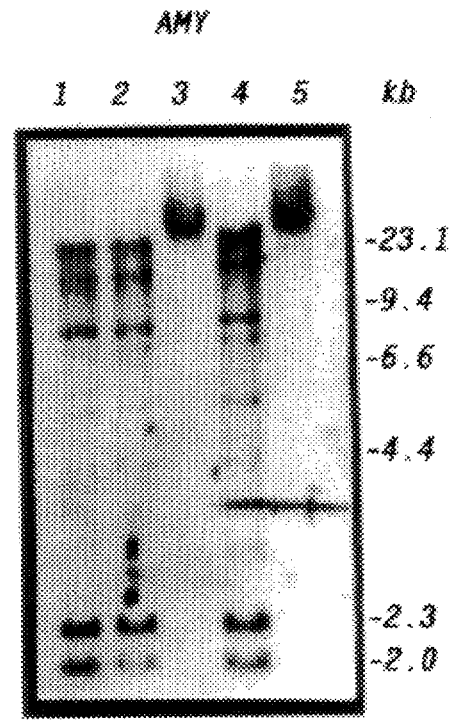

DNA was isolated from the 3DG cell line and from a non-transformed control cell line, digested with BamHI and subjected to Southern blot hybridization (GUS Panel, FIG. 3A, and AMY Panel, FIG. 3B). When the blot was probed with the GUS gene, a strong hybridization signal to DNA from the 3DG cell line (lanes 2–5; FIG. 3A) was observed. No hybridization was seen with DNA isolated from the control cell line (panel GUS, lane 1 of FIG. 3A). The negative result in the GUS panel (lane 1) was not due to the lack of DNA transferred to the membrane. Equivalent amounts of DNA were detected in all lanes when the same membrane was stripped of the GUS probe and rehybridized with a probe from the rice α-amylase gene RAmy1A (Amy panel; FIG. 3B). These bands hybridizing to the α-amylase probe have the molecular weights predicted from the DNA sequence of the RAmy1A gene. Using the GUS probe, the 3DG cell line had the same hybridization pattern before (GUS panel, lane 2) and after (lane 4) the two cycles of single cell clump selection, indicating that the plasmid DNA was stably inherited as the cells proliferated.

Two types of structural evidence indicate that the RAmy3D/GUS DNA is integrated into the chromosomes of the 3DG cell line. First, Southern blot analysis revealed that the GUS gene probe hybridized exclusively to undigested genomic DNA larger than the size of the p3DG plasmid (GUS panel, lanes 3 & 5). Second, digestion of the DNA from the 3DG cell line with endonuclease BamHI resulted in multiple hybridization bands (GUS panel, lanes 2 & 4). BamHI does not cut within the RAmy3D/GUS gene construct, so each band size represents a different sized junction fragment between the unique BamHI site in the p3DG plasmid and a BamHI site in the adjacent chromosomal DNA. Thus, multiple copies of the RAmy3D/GUS gene construct (and at least one copy of the hygromycin-resistance gene) have been integrated into the genome of the 3DG cell line. The low molecular weight bands and the faint bands of hybridization on the Southern blot probably represent fragments of the RAmy3D/GUS gene construct inserted into the rice genome.

Metabolic regulation of RAmy3D/GUS in transgenic rice cell lines

Gene expression and enzyme activity for GUS was assayed in the 3DG cell line to determine whether the promoter fragment in the RAmy3D/GUS construct contains all of the cis-elements necessary for proper-expression and metabolic regulation of the gene. Dot-blot hybridization using a GUS gene probe indicated that the mRNA level from the GUS gene in 3DG cells increased as sugar was depleted from the culture medium (data not shown).

Figure 4:
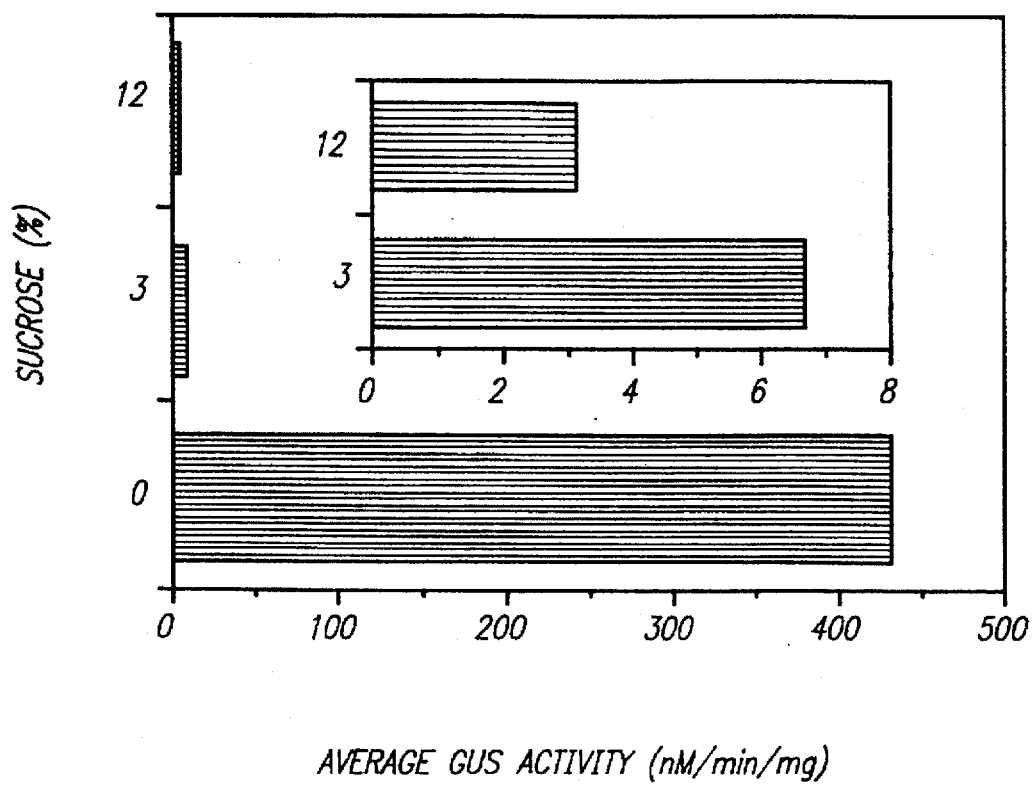
FIG. 4 provides the results of a fluorescent assay detecting GUS.

The GUS enzyme assay was used to test for the expression of RAmy3D/GUS in response to various concentrations of sucrose in the culture medium. The 3DG cell line was subcultured into modified AA medium containing 0%, 3% or 12% sucrose. Three days later, water soluble protein was extracted and assayed for GUS by the fluorescence assay (FIG. 4). The GUS activity in cells cultured with no sucrose was 65-fold higher than that of cells grown in 3% sucrose and 130-fold higher than that of cells grown in 12% sucrose. Thus, the transcriptional activity of the RAmy3D promoter was greatly repressed in the presence of high levels of sucrose while being highly induced under conditions of sugar deprivation.

Figures 5, 6D:
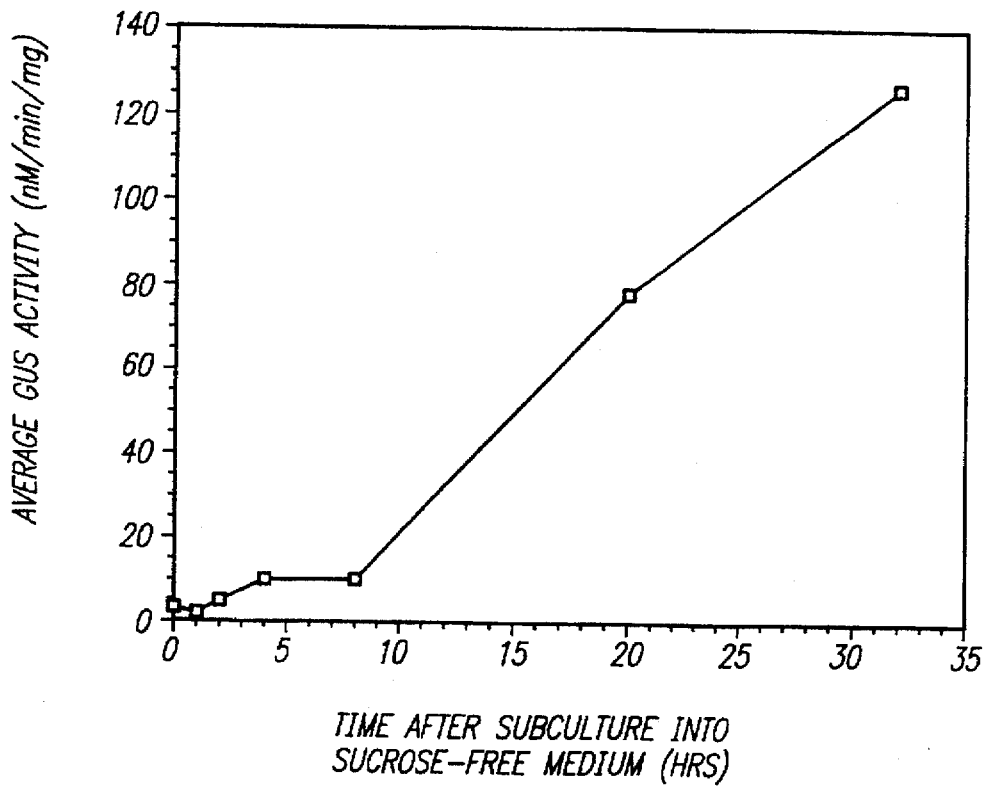
FIG. 5 provides the results of a fluorescent assay detecting GUS from cells free of sucrose.
FIG. 6D is a table comparing sequence homology between α-amylase promoters.

The timing of RAmy3D promoter induction in response to sugar deprivation was studied by incubating 3DG cells in sucrose-free medium. There was little or no increase in GUS activity during the first eight hours of incubation (FIG. 5). GUS activity increased rapidly between eight to thirty-two hours after subculturing. The expression and metabolic regulation of the RAmy3D/GUS gene construct resembles that of the endogenous RAmy3D gene. Our results are similar to others who observed an increase in total α-amylase mRNA beginning 4 hours after the start of sugar deprivation. Thus, the cis-element(s) responsible for metabolic regulation must be contained in the 942 bp promoter region on the RAmy3D/GUS construct.

The expression of the GUS gene product was visualized using histochemical staining methods (Jefferson supra) as seen in FIG. 1A where cell cultures incubated in the absence of sugar show blue staining with relatively high blue staining evident and where 3% sugar repressing the expression of the GUS gene product with relatively less blue staining is evident.

Promoter sequence analysis

Figure 6A:
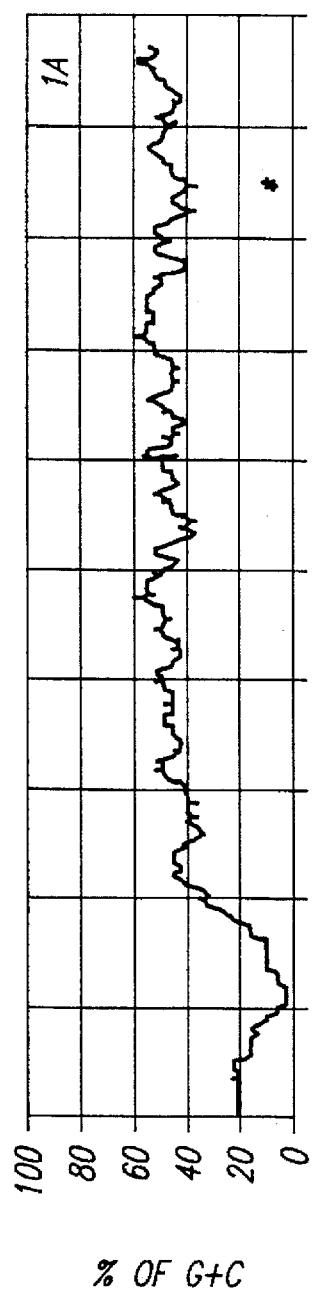
FIGS. 6A to 6C provide a comparison of G+C content for three different α-amylase promoters.
Figure 6B:
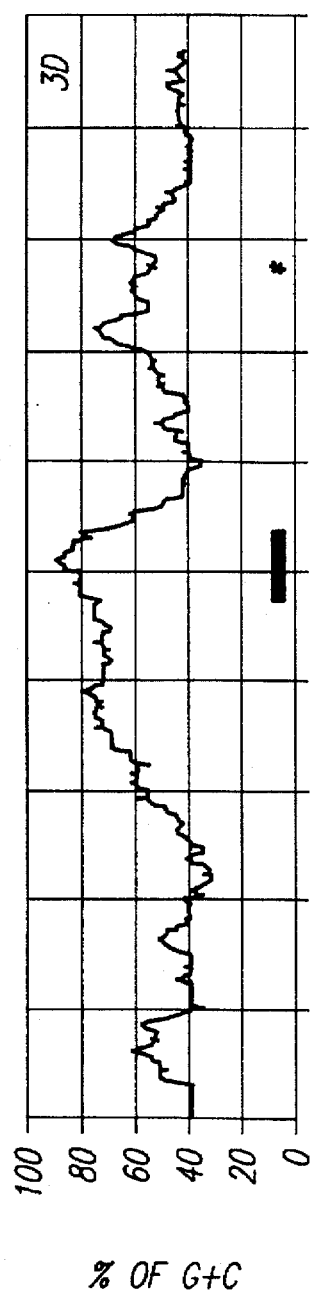
Figure 6C:
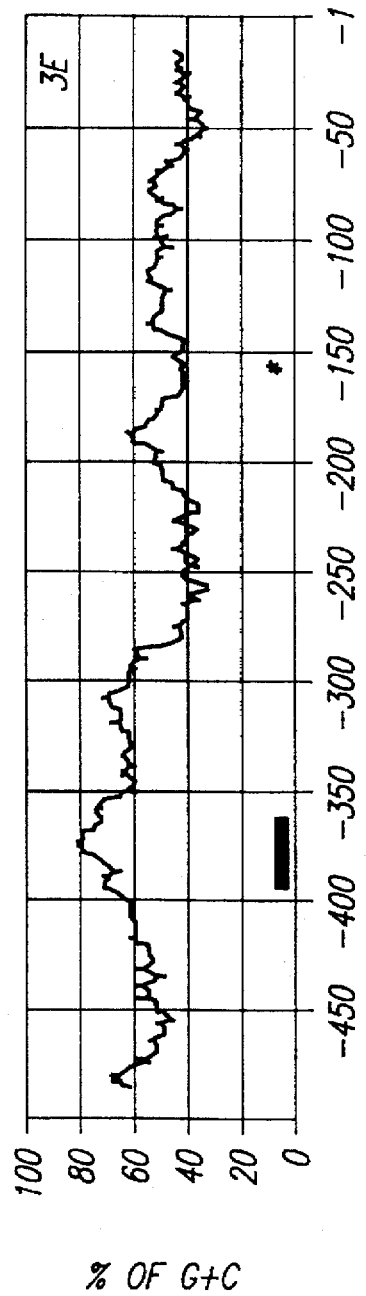

Promoter sequences for RAmy3D and RAmy3E were compared to gain additional insight into the metabolic regulation of these genes. Two regions of sequence similarity were previously identified in the promoters of these genes. One of these regions consists of a 31 bp GC-rich sequence that is 71% identical between the RAmy3D and RAmy3E genes (FIGS. 6B and 6C, respectively). This sequence is not found in the RAmy1A promoter (FIG. 6A) or in any other rice α-amylase promoter (data not shown). This sequence is found at position −264 in RAmy3D (FIG. 6D) and contains three nearly perfect repeats of a hexanucleotide sequence composed solely of G and C residues. The RAmy3E promoter contains one complete and one partial copy of the hexanucleotide repeat sequence. The tandem duplication of GC-rich hexanucleotides in the 31 bp GC-rich sequences is reminiscent of binding sites for the mammalian transcription factor Sp1. An 11 bp sequence containing part of the GC-rich hexanucleotide is also found in the RAmy3D and RAmy3E promoters (FIG. 6D). These sequences may represent cis-acting elements involved in the metabolic regulation of the rice α-amylase genes. GC-rich promoter sequences have also been identified in the metabolically regulated α-amylase genes of *Aspergillus oryzae*.

Example 2

Secretion of heterologous protein across the aleurone layer of an intact rice seed using the RAmy1A promoter Experimental procedures Plasmids Plasmids were constructed using standard recombinant DNA methods (Ausubel et al., 1989, *Current Protocols in Molecular Biology*, N.Y. John Wiley and Sons and Sambrook et al., supra, 1989). The RAmy1A gene of rice was chosen because of its responsiveness to GA (O'Neil et al., 1990 *Mol. Gen Genet.*, 221, 235–224) and because it is the most active of the α-amylase genes expressed during seed germination (Karrer et al., 1991, *Plant Mol. Biol.*, 16, 797–805). Two regions of the RAmy1A promoter were fused to the gus A reporter gene to produce plasmids pH4/GUS (−748 to +31) and pE4/GUS (−232 to +31). Both promoter regions contain three conserved sequences ($^{-214}$CCTTTT$^{-209}$, $^{-147}$TAACAAA$^{-141}$, and $^{-130}$TATCCAT$^{-124}$) found in all the GA-responsive cereal α-amylase genes examined to date (Huang et al., 1990). An additional pyrimidine box is present in pH4/GUS at position −312.

The promoter for the RAmy1A gene was subcloned as a 2.3 kb DNA fragment from the rice genomic DNA clone (lOSg2) into pBluescript M13+KS. The nucleotide sequence of this promoter has been described in Huang et al., 1990 *Nuc. Acids Res.* 18:7007–7014. The principal features of these constructs consists of the b-glucuronidase gene (gusA), together with the transcriptional terminator of the nopaline synthase gene from pBI101 as reported in Jefferson, 1987 *EMBO Journal* 6:3901–3907.

The expression cassette was inserted into the SmaI site of pBluescript and designated pBSGUS. RAmy1A(promoter)/gusA gene fusions were constructed by inserting restriction fragments containing the RAmy1A promoter into pBSGUS. The restriction fragments used to make constructs were the PstI-HindIII fragment (−748 to +31, pH4/GUS) and the PsfI-EcoRI fragment (−232 to +31, pE4/GUS). The coordinates used to describe these restriction fragments are based on transcription start point for RAmy1A (Huang et al., supra 1990).

Rice Transformation

RAmy1A/GUS plasmids were cotransformed into rice protoplasts (*Oryza sativa L. japonica varieties*, Nipponbare, Kinuhikari and Toride-1) by electroporation as described by Shimamoto et al., 1989, Fertile transgenic rice plants regenerated from transformed protoplasts, *Nature*, 338:274–276 and Kyozuka and Shimamoto, 1991 Transformation and regeneration of rice protoplasts, in *Plant tissue Culture Manual* (Lindsey, K. ed). Dordrecht:Kluwer Academic Publishers B1:1–16. The hph gene (hygromycin phosphotransferase) was used as the selectable marker in these studies. Hygromycin B resistant calli were screened for GUS activity by incubating a portions of calli with X-glucuronide solution (Jefferson, 1987 supra). GUS positive calli were further cultured and plants were regenerated from these callus cultures.

Southern blot analysis

The GUS positive R1 plants, derived from two lines each of H4/GUS and E4/GUS primary transgenic lines, were used for Southern blot analysis. Total genomic DNA was isolated from mature leaves, digested by the restriction enzyme EcoRI and transferred onto a positively charged nylon membrane (Amarsham). The coding region of the gusA gene was labeled and amplified with digoxigenin11-dUTP by polymerase chain reaction and used for probing the intact RAmy1A/gusA genes. Hybridization and chemiluminescence signal detection were performed according to manufacturer's specifications (Boeringer Mannheim Biochemica).

GUS assays

For histochemical analysis of GUS activity, germinating seeds were hand-cut with a razor and stained with X-glucuronide solution (5-bromo-4-chloro-3-indolyl glucuronide) as previously described in Kyozuka et al., 1991 supra and Terada et al., 1993, *Plant J.* 3:2412–252. For quantitative analysis, crude extracts from transgenic rice seeds were used for fluorometric assays of GUS activity as described previously (Kyozuka et al., 1991; Terada et al., 1993). For developmental studies, transgenic R1 seeds were pealed off, sterilized with 10% NaOCl for 10 min and washed with distilled water. Seeds were germinated in plastic wells containing water for 2, 4, 6, and 8 days at 30° C. under light. For quantitative measurements of GUS activity germinating seeds were divided into the embryo and endosperm portions. In the case of the embryo, residual amount of endosperm, roots and shoots were removed before the assay. For the analysis of hormonal regulation of the RAmy1A/gusA chimeric genes, transgenic R1 seeds were deembryonated and the embryoless seeds and sliced longitudinally into three pieces. Each slice was treated with acetate buffer (10 mM sodium acetate pH 5.2), $10^{-7}$M GA3 in acetate buffer, $10^{-7}$M GA$_3$ and $10^{-5}$M ABA in acetate buffer, for 4 days at 30° C. in the dark. Treatment slices were then used for the histochemical and the quantitative GUS assays.

Results

Southern blot analysis of transgenic rice plants

Figures 7A, 7B, 7C:
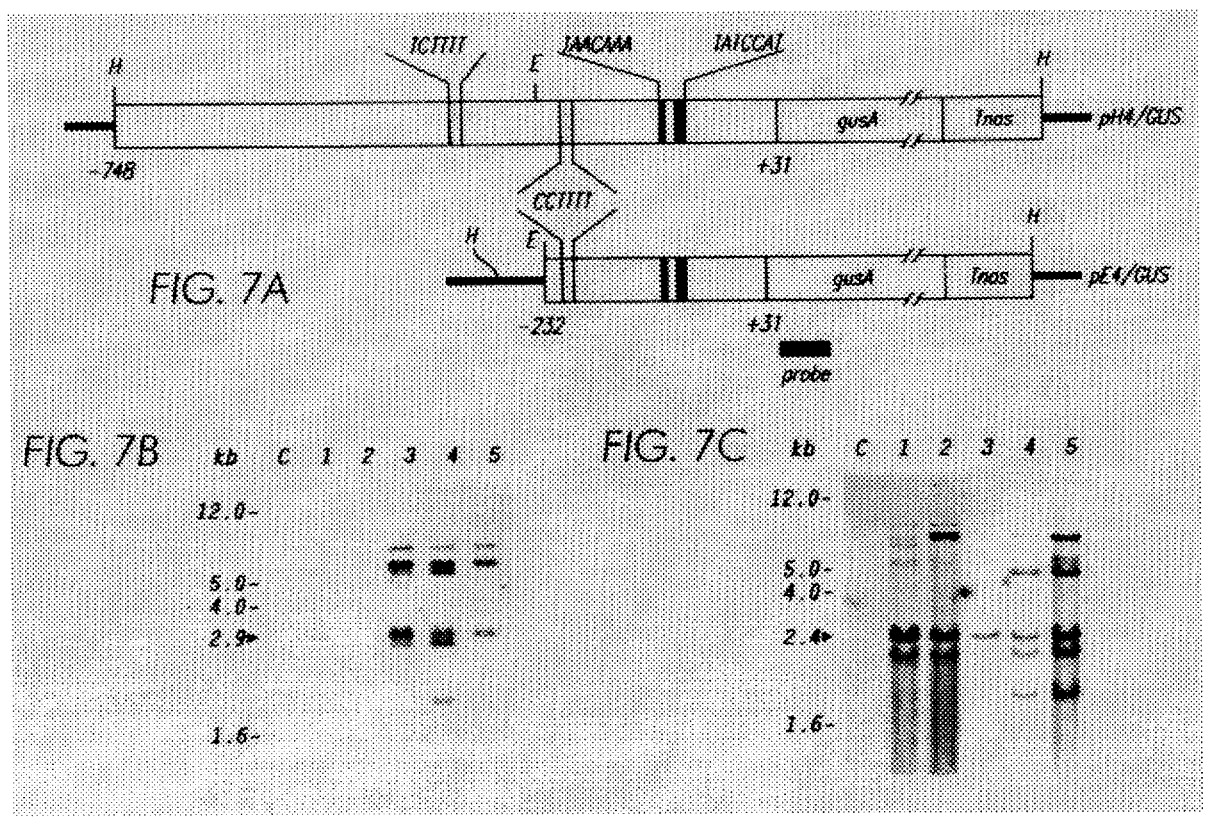
FIGS. 7A–7C.

Southern blot analysis confirmed the presence of H4/GUS and E4/GUS gene fusions in the rice genome using the coding region of gusA as a probe (FIG. 7A). The results indicated that complete sequences of the H4/GUS and E4/GUS chimeric genes were present in transgenic plants and that the gusA gene was stably transmitted to the progeny (FIG. 7B and 7C). In addition to the complete copies of the transgenes, several rearranged copies were also detected. The copy number of intact chimeric genes was estimated to be 1–3 per haploid genome.

GUS activity in transgenic rice seeds

Figure 8B:
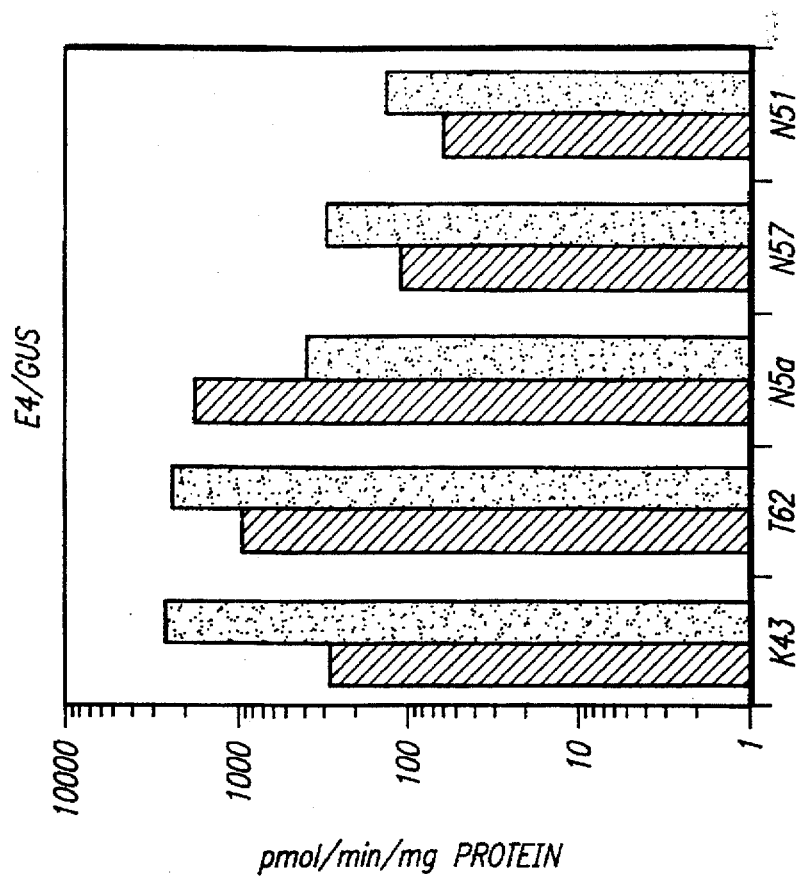
FIGS. 8A, 8B are fluorometric measures of the expression of GUS using the H4 and E4 constructs in different transgenic rice seed.
Figure 8A:
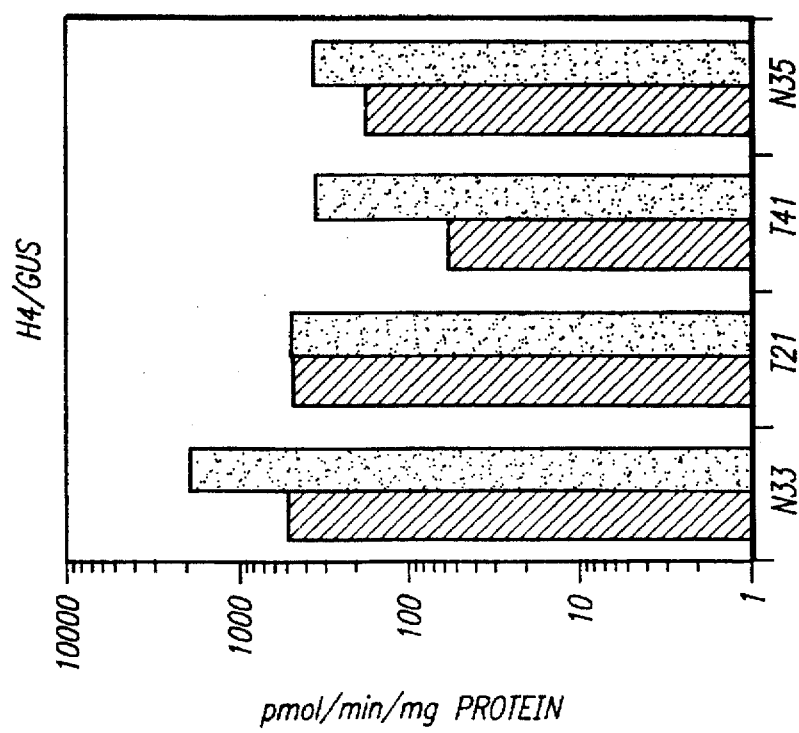

To compare the relative expression levels of the H4/GUS and E4/GUS genes, the embryos and endosperms of germinated transgenic seeds were separated and the GUS activity in each tissue was measured fluorometrically (FIGS. 8A and 8B, respectively). GUS assays of endosperm tissue were performed at 6 days of germination, the time when α-amylase expression in the aleurone layer is at its highest (FIGS. 9A to 9D). Histochemical examination of 6-day germinated seeds showed that GUS activity was restricted to the scutellum of the embryo and the aleurone layer of the endosperm. In all four lines transformed with the H4/GUS gene, the aleurone activity was higher than the scutellum activity (FIG. 8A). Similarly, four of the five lines transformed with E4/GUS gene showed GUS activity to be higher in the aleurone than in the scutellum (FIG. 8A). Comparisons between H4/GUS and E4/GUS transformed lines, revealed no significant differences in GUS activity in the scutellar and aleurone tissues.

Temporal and spatial regulation of RAmy1A/GUS expression during germination of transgenic rice seeds To investigate the role of the RAmy1A promoter in the temporal and spatial expression of heterologous genes during rice seed germination, histochemical and quantitative GUS assays on transgenic seeds were performed. Histochemical analysis of the H4/GUS chimeric gene showed that GUS activity could be detected in the scutellar epithelium after 2 days of germination and that this activity spread into the adjacent aleurone layer by day 4. On day 6, the GUS expression in the aleurone layer increased to the extent that it covered all portions of the seed.

Figure 9B:
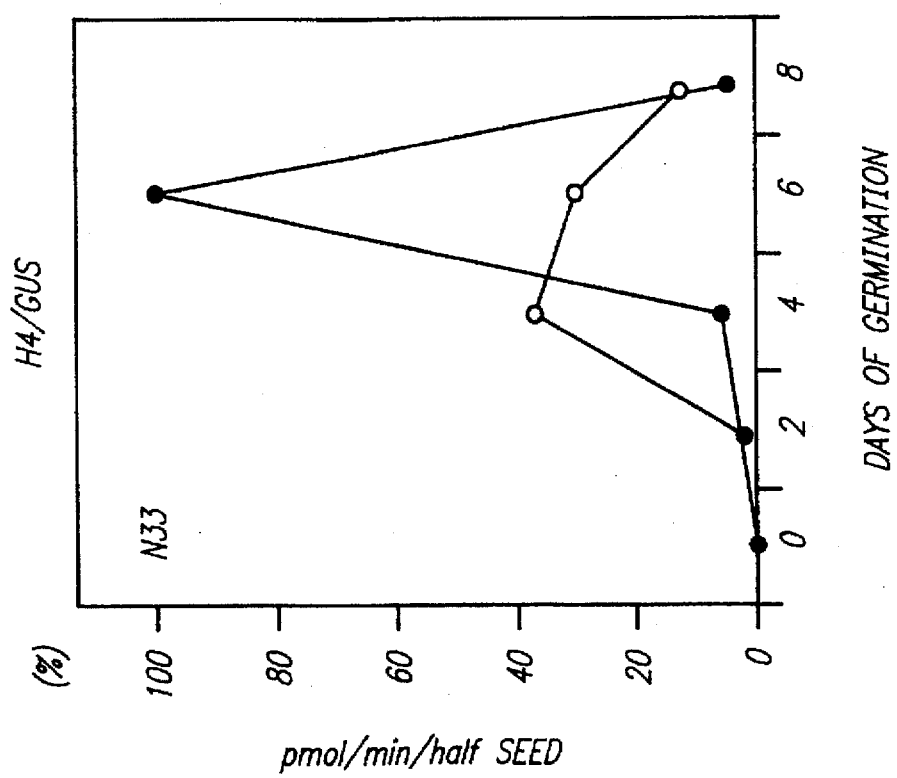
FIGS. 9A, 9B, 9C, and 9D are depictions of fluorometric measures of the expression of GUS in four transgenic rice seed lines using both the H4 (FIGS. 9A and 9B) and E4 (FIGS. 9C and 9D) GUS constructs.
Figure 9A:
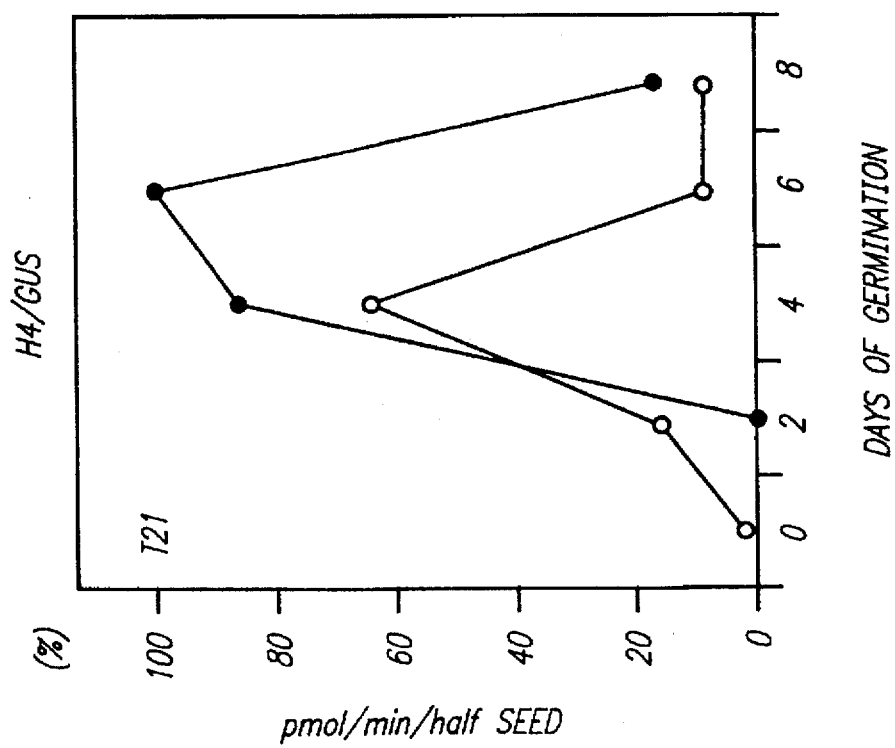

To quantify the levels of GUS activity revealed by histochemical analysis, the GUS activities of germinating seeds derived from two H4/GUS transgenic lines (T21 and N33) were measured (FIGS. 9A and 9B, respectively). Scutellar GUS activity (open circles) appeared on day 2, peaked on day 4 and decreased thereafter.

Figure 9D:
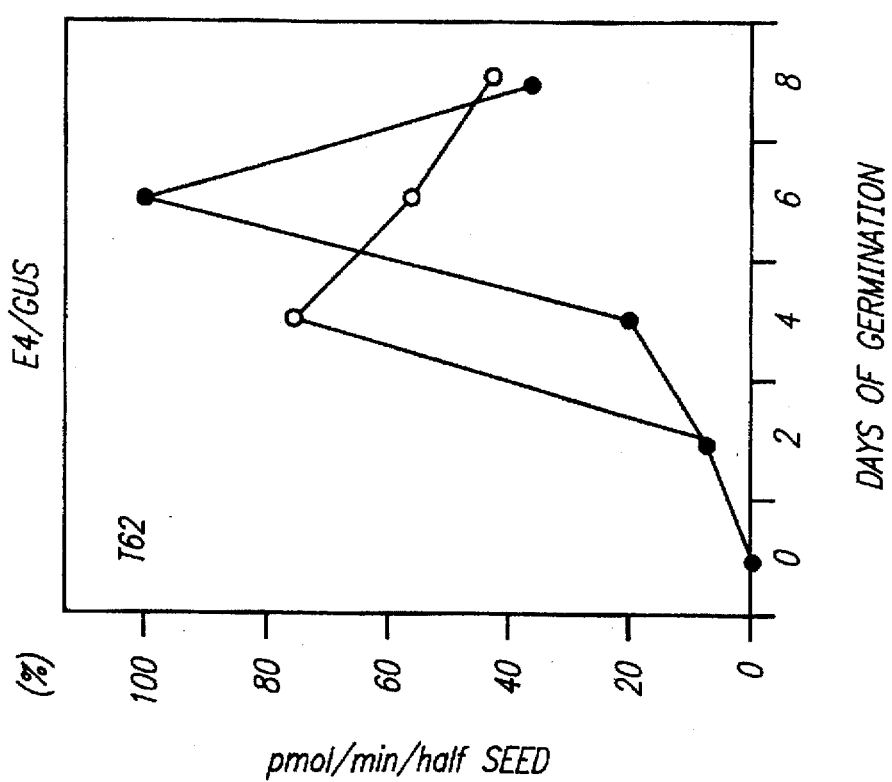
Figure 9C:
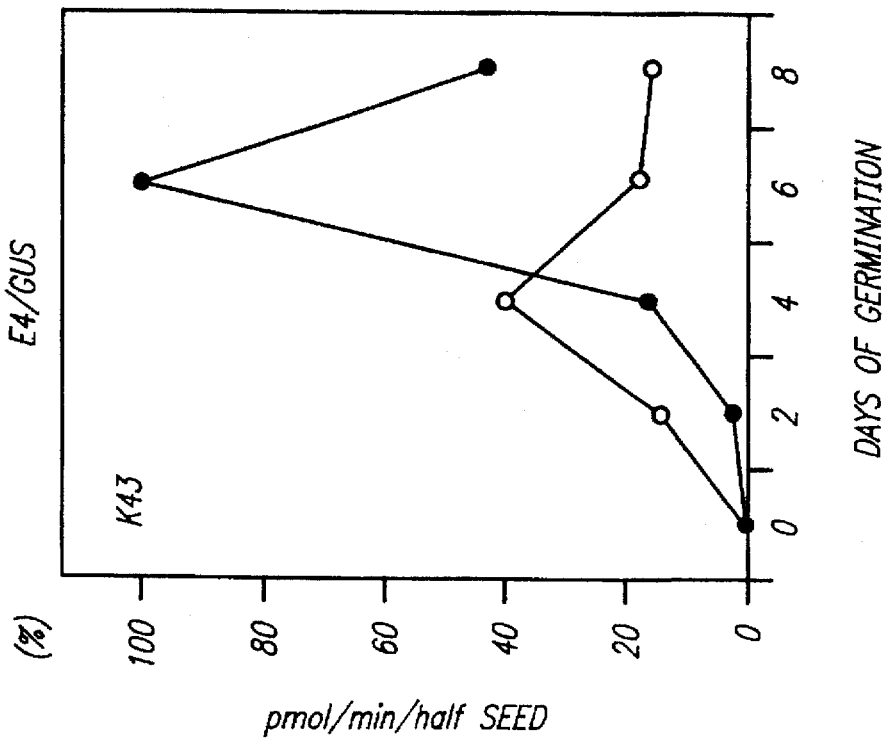
Figure 10D:
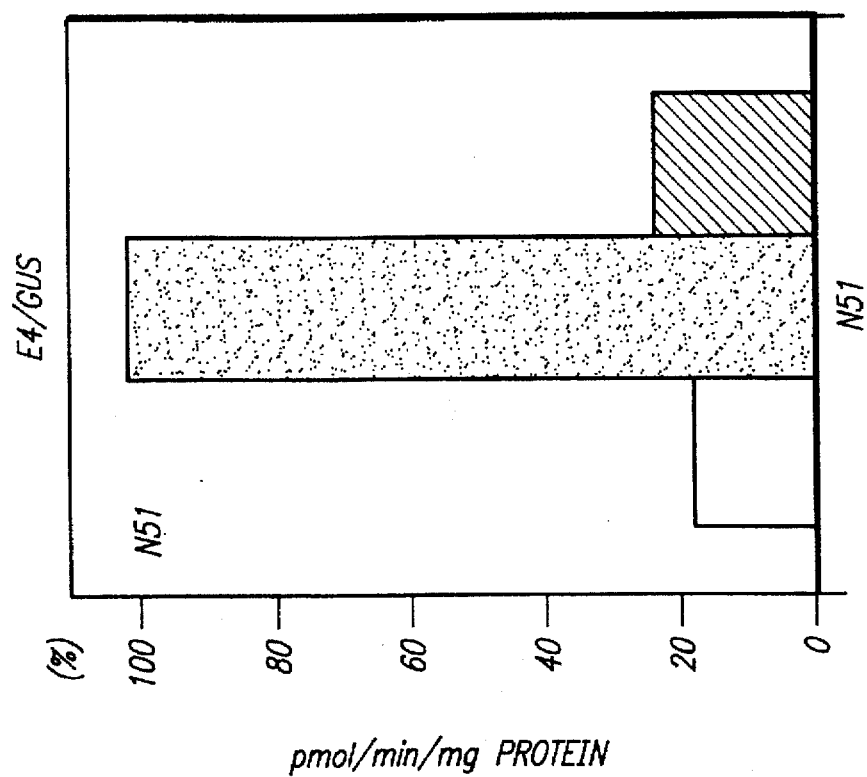
Figure 10C:
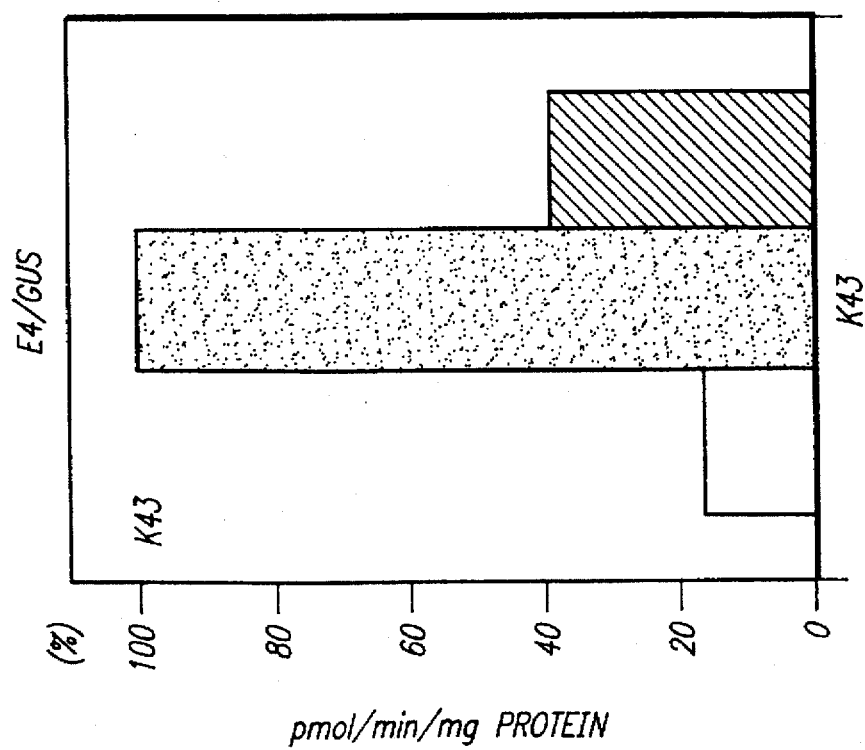

In contrast, aleurone GUS activity (closed circles) was first detected on day 4, peaked on day 6 and decreased sharply by day 8. These results clearly show that the RAmy1A1GUS fusion genes are differentially regulated in scutellum and aleurone tissues during rice seed germination. Similar experiments were performed on seeds from two lines of rice (K43 and T62) transformed with the E4/GUS gene fusion (FIGS. 9C and 9D, respectively). Histochemical assays revealed patterns of expression nearly identical to those observed for the H4/GUS gene. Quantitative assays of GUS activity in the scutellar and the aleurone layers of germinated seeds indicated that the E4/GUS gene is expressed in the scutellum on day 2 and peaks at day 4. GUS activity in the aleurone layer is first detected at day 4 and peaks on day 6 (FIGS. 9C and 9D). These results show that the −748 to +31 region in the H4/GUS gene and the −232 to +31 region in the E4/GUS gene, function identically with respect to the localization of expression and the developmental regulation during seed germination.

Hormonal regulation of the RAmy1A/GUS genes in the aleurone layer of transgenic rice seeds To examine effects of exogenously GA and ABA on the expression of the H4/GUS and E4/GUS genes in seeds, deembryonated seeds were cut into three slices and each slice was treated with GA or a combination of GA and ABA. The histochemical examination of the H4/GUS seed slices treated with GA-free buffer showed no GUS activity. However, seed slices treated with GA showed GUS activity in the aleurone layer. The observed induction of the GUS expression by GA was suppressed by addition of ABA. Similar GA induction of GUS in the aleurone layers of pE4/GUS transformed seeds was also observed (data not shown).

In an attempt to quantify GA induction of the RAmy1A promoter in transgenic seeds, GUS activity was measured for both GA, and GA+ABA treated seeds (FIGS. 10A to 10D). A 10 to 40-fold increase in GUS activity was observed after GA treatment Of H4/GUS and E4/GUS seeds. When ABA was added along with GA, the GUS activity was suppressed to a level just above background. The degree of GA induction and ABA suppression was similar for both H4/GUS and E4/GUS derived seeds.

Example 3

Secretion of GUS into the media using the RAmy1A promoter in transgenic rice cells.

The suspension cells of example one are removed by filtration and the filtered media is assayed for GUS activity. The assay methods are as stated in Example 1.

---

What is claimed is:

1. An isolated DNA sequence, comprising a transcriptional initiation region obtained from the nucleic acid sequence consisting of SEQ ID NO:1.

2. An isolated DNA sequence of claim 1, where said transcriptional initiation region is operably linked to a heterologous gene.

3. An isolated DNA sequence of claim 1, where said transcriptional initiation region is inducible during seed germination.

4. An isolated DNA sequence of claim 2, where said transcriptional initiation region is operably linked to a nucleic acid encoding a signal sequence, where said signal sequence is suitable to facilitate secretion of a product of the heterologous gene across an aleurone or scutellar epithelium layer into the endosperm of a seed.

5. An isolated DNA sequence of claim 4, where said signal sequence is operably linked to a heterologous gene that is followed by a transcriptional termination sequence.

6. An isolated DNA sequence of claim 4, wherein the signal sequence is from an $\alpha$-amylase gene.

7. An isolated DNA sequence of claim 6, wherein the amylase gene is selected from the group consisting of RAmy1A (SEQ ID NO:2), RAmy3B, RAmy3C, RAmy3D, HV18 (SEQ ID NO:1) and RAmy3E.

8. An isolated DNA sequence of claim 2, wherein the heterologous gene encodes a protein selected from the group consisting of an antibody, an enzyme, a hormone, and a viral protein.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 820 base pairs
        ( B ) TYPE: nucleic acid
        ( C ) STRANDEDNESS: single
        ( D ) TOPOLOGY: linear ( i i ) MOLECULE TYPE: DNA (genomic)

(ix) FEATURE:
    (A) NAME/KEY: misc_feature
    (B) LOCATION: 1..820
    (D) OTHER INFORMATION: /standard_name= "HV-18"

(xi) SEQUENCE DESCRIPTION: SEQ ID NO:1:

| | | | | | | |
|---|---|---|---|---|---|---|
| GGATCCTAGC | TACGGACAGC | GCCCCGGTTA | TGGAGGCCGA | CAGCCGCGGC | GCGCGGCTGC | 60 |
| GTAGCAGTGC | AGCGTGAAGT | CATAGATAGA | CTGTAGAGGG | CATGGCGGCA | AGTGAAAACA | 120 |
| CACTTCCGTT | TGTTCTGTTG | AGTCAGTTGG | ATCTGCTTTG | GCCTGGCGAT | AACGTCTCCG | 180 |
| GCCATTGTTT | ATCACGGCGC | CTGCTTATCC | CTCCGAAAGT | TTGAGCAAAA | GGTGCAGCTT | 240 |
| CTTTCTAGTA | CAGAAATGAC | GTCCAGAGTT | GCAGCAACCC | ATTCGGAACT | CCTGGTGGAT | 300 |
| GCCAACGAAA | TTAAATGGGA | TAAAACTTAG | TGAAGAATCT | ATATTTCTT | GCAACAACAT | 360 |
| ACTCCTACCC | TCACGAATTG | AATGCTCATC | GAACGAATGA | ATATTGGAT | ATATGTTGAT | 420 |
| CTCTTCGGAC | TGAAAAAGTT | TGAACTCGCT | AGCCACAGCA | CACTATTCCA | TGAAAAATGC | 480 |
| TCGAATGTTC | TGTCCTAGAA | AAACAGAGGT | TGAGGATAAC | TGACGGTCGT | ATTGACCGGT | 540 |
| GCCTTCTTAT | GGAAGGCGAA | GGCTGCCTCC | ATCTACATCA | CTTGGGCATT | GAATCGCCTT | 600 |
| TTGAGCTCAC | CGTACCGGCC | GATAACAAAC | TCCGGCCGAC | ATATCCACTG | GCCCAAAGGA | 660 |
| GCATTCAAGC | CGAGCACACG | AGAAAGTGAT | TTGCAAGTTG | CACACCGGCA | GCAATTCCGG | 720 |
| CATGCTGCAG | CACACTATAA | ATACTGGCCA | GACACACAAG | CTGAATGCAT | CAGTTCTCCA | 780 |
| TCGTACTCTT | CGAGAGCACA | GCAAGAGAGA | GCTGAAGAAC | | | 820 |

(2) INFORMATION FOR SEQ ID NO:2:

(i) SEQUENCE CHARACTERISTICS:
        (A) LENGTH: 2389 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..2389
        (D) OTHER INFORMATION: /standard_name= "RAMY-1A"

(xi) SEQUENCE DESCRIPTION: SEQ ID NO:2:

| | | | | | | |
|---|---|---|---|---|---|---|
| CTGCAGGCAT | GCGAGAGGCA | CGGGGTTCGA | TTCCCCGCGT | CTCCATCGGC | ACTGTTTTT | 60 |
| AACATCAAAC | GCTGTTCGAT | CCACTATCTG | TTAATTTCGC | AAACACAACT | AAATCTTTTT | 120 |
| TTTTTTTTGC | CGGTGCGTGC | AGTGTGACGT | CCAAGGCATG | GCGCATTGGC | GCCTCCCCTC | 180 |
| TTTCCCTTGA | TCTTTTCATC | AGTTCGTTCT | TCTTGCAGAA | AAGCTGTTCT | GTTAAGTCGG | 240 |
| TTCCGATCTG | CTCTTGGGCT | CTTGCCAGAA | ACAACCTGTG | TACGCCAGAC | TTATCAAGCC | 300 |
| AACCATCCTG | ATGAGCCTCT | GCTTATACAA | GCCTTTGACT | CCAAAAGGA | CGAGGAGGCT | 360 |
| TGCAGCCGCA | CGGAAATAAG | CCGACCGATC | CTTTATTGCT | CTATCTTTTT | CCCTTGGAAT | 420 |
| AAAAAACAGC | CCAATTAAAA | TCTGGGATGA | AACTATGGCT | AGCTGTTCGC | GGTGTCAGTT | 480 |
| CTCGGGACGC | TACCGTTGTT | TTGTTTGAAC | CGGAATGTTC | AGGGCGGTTC | ACACCATAGA | 540 |
| CTTGGAGCCA | AGTGGTTCCA | TCCACAAAAT | TTTCTCATCT | TGAATATTCT | GTTATCTGCC | 600 |
| TCGACAGACG | CACCATATCC | TGTGTTCAGG | AATGAATGTG | CTACAGCCAA | CGTGCTGCAT | 660 |
| GAAATTTGCT | GAAATCGTGC | TAAAATGTGC | ATGGCAACAG | GAACCTGATG | CCCTGGTCCT | 720 |
| GTGGAACTGC | CACGGGAAAG | TATTTTTTAT | AGCTAGGTGC | AATCGTATCT | AGGTGTATAC | 780 |
| ATGTCACCTA | CATAGCTACT | CCCCTTTATC | TTAAAATATA | ATAATTTTA | ACTCTCAGTA | 840 |

| | | | | | | |
|---|---|---|---|---|---|---|
| TTTGTCCTAA | AATATAACAA | ATTCTCCATC | AACATTATCT | TCCCAACCAA | TCACAACCCT | 900 |
| TCATCATTAA | TTTTTCCCC | CTACCTCCAC | TACTCATCTA | ATCACAACCC | TCCAACACTC | 960 |
| ACTTCTATCT | ACTTTCTTAA | TAACTGTCTT | CAACCCTAAA | ACTTCTTATA | TTTTAGGACG | 1020 |
| GAGGGAGTAT | CTAAATATTT | CATAAAAAAA | ATGTTAAGAT | AGATAAAGAA | GATATAAACC | 1080 |
| CACTATGCAA | ACATGCACAT | CAAAATTTAA | TTTACAGTAA | AGAAACAGAA | ATAACATATT | 1140 |
| CTATTTGTGC | TGGAGATGTA | CTGTTCACAA | TATTGTTTTT | TTATTTTTA | TTTATCTGAT | 1200 |
| TATATATCTG | TTTCAGCCTT | GCATGGTTGT | GTATGTTTGT | GTATAGACTT | ATGCCATTGT | 1260 |
| GATTGATGCT | ACCAATTATT | TTCAGACTAT | TTTTTATAG | AGGAATTTTA | TAGTTCTTGA | 1320 |
| GAAAATACCT | TGAAGTATCT | AAATTTTACA | CTAAAATTGT | TGGTACCTTG | AGGTACAAAG | 1380 |
| TACCTAGAGG | TACCAAATTT | TACTAGAAAA | TTGTGGCACC | TTTAGGTACC | TTCTCAAAAA | 1440 |
| TAGTACAATT | ATGGGCCGTT | TTGGATTTAG | TGCCAAAACG | TGCTCTACAA | ATATTTGAT | 1500 |
| AGTTTGAACA | GTGCATAAGA | CGGGTTTGGT | TTGAAGCCAA | ATCATTGGCA | TTGCCAATGT | 1560 |
| CCAATTTGAT | ATTTCTATA | TTATGCTAAA | AGCTTGGTTC | TAAATTGGCC | TCCAACCAAA | 1620 |
| TACAACTCTA | CTCTACCAAA | AAATTTGTAG | TGCCAAAACT | TGCCTAGGTT | TTGTCACTAC | 1680 |
| CAACATTTTG | GTAAGTATTA | AACCAAACAA | GCCCTACATT | TTTTTATGTA | CATTTAAGTT | 1740 |
| GTATGTAAAT | GATGGGTGCG | GTTGCACCTA | GGTGAAAAAA | AATACATATT | CGCCACAACT | 1800 |
| CGCAACATGT | ACCAATTCAG | CAGCAAGTGT | AAGAGAGAAG | ATTTCTCTCG | TTTTACACGC | 1860 |
| GCACGTTCAA | TTCCTGAACT | ACTAAACGGT | ATGATTTTT | GCAAAAATTT | TCTATAGGAA | 1920 |
| AGTTACTTAA | AAATTATATT | AATCTATTTT | TAAAATTTAA | AATAGTTAAT | ACTCAATTAA | 1980 |
| TTATACGTTA | ATGGCTCAGC | TCGTTTTGCG | TACATTCTCA | ATCGATTCTT | TTCCTCTGCT | 2040 |
| CTCAAATGCT | CTGTGTGCGA | TCAGGTATTC | ATGTTCAGCT | CGCACAAGCA | CAAGCAAGAC | 2100 |
| AGATGGAATT | CCTACTGACC | TGCGCCTTTT | GAGTCGCTCC | AACTCTCAAA | GTCTCAAGGC | 2160 |
| CATTAAATTG | CCTATGGGCT | CACCAGCCAA | TAACAAACTC | CGGCTGTTAT | CCATCCAATC | 2220 |
| CAGTGTCCCA | AAGCAACATT | CAAGCCCAGC | CAGGCCTCCA | AAAGTTGCAA | GTTGAGCATG | 2280 |
| GCAAAATCCC | CGGCAATTCT | CGACTATAAA | TACCTGACCA | GACACACCCA | GGAGCTTCAT | 2340 |
| CAATCATCCA | TCTCCGAAGT | GTGTCTGCAG | CATGCAGGTG | CTGAACACC | | 2389 |

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..31
        ( D ) OTHER INFORMATION: /standard_name= "31 bp RAmy3D"

( x i ) SEQUENCE DESCRIPTION: SEQ ID NO:3:

GAGACCGGGC CCCGACGCGG CCGACGCGGC G                                     31

( 2 ) INFORMATION FOR SEQ ID NO:4:

( i ) SEQUENCE CHARACTERISTICS:
        ( A ) LENGTH: 31 base pairs
        ( B ) TYPE: nucleic acid
        ( C ) STRANDEDNESS: single (D) TOPOLOGY: linear (ii) MOLECULE TYPE: DNA (genomic)

(ix) FEATURE:
            (A) NAME/KEY: misc_feature
            (B) LOCATION: 1..31
            (D) OTHER INFORMATION: /standard_name= "31 bp RAmy3E"

(xi) SEQUENCE DESCRIPTION: SEQ ID NO:4:

GAGAGCTCGC GCCGCCTCGA TCGGCGCGGC G                                      31

(2) INFORMATION FOR SEQ ID NO:5:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..11
            (D) OTHER INFORMATION: /standard_name= "11 bp RAmy3D"

(xi) SEQUENCE DESCRIPTION: SEQ ID NO:5:

TTCCGGCTTG C                                                            11

(2) INFORMATION FOR SEQ ID NO:6:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..11
            (D) OTHER INFORMATION: /standard_name= "11 bp RAmy3E"

(xi) SEQUENCE DESCRIPTION: SEQ ID NO:6:

TTGCGGCTTG C                                                            11

(2) INFORMATION FOR SEQ ID NO:7:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..12
            (D) OTHER INFORMATION: /standard_name= "Taka-amylase"

(xi) SEQUENCE DESCRIPTION: SEQ ID NO:7:

CGGCCCGTCG GC                                                           12